US007384908B1

(12) United States Patent
Brenneman et al.

(10) Patent No.: US 7,384,908 B1
(45) Date of Patent: Jun. 10, 2008

(54) ORALLY ACTIVE PEPTIDES THAT PREVENT CELL DAMAGE AND DEATH

(75) Inventors: Douglas E. Brenneman, Damascus, MD (US); Catherine Y. Spong, Arlington, VA (US); Illana Gozes, Ramat Hasharon (IL); Albert Pinhasov, Tel Aviv (IL); Eliezer Giladi, Ramat Poleg (IL)

(73) Assignee: National Institute of Health, Rockville, MD (US)

( * ) Notice: Subject to any disclaimer, the term of this patent is extended or adjusted under 35 U.S.C. 154(b) by 620 days.

(21) Appl. No.: 10/049,587

(22) PCT Filed: Aug. 17, 2000

(86) PCT No.: PCT/US00/22861

§ 371 (c)(1),
(2), (4) Date: Feb. 12, 2000

(87) PCT Pub. No.: WO01/12654

PCT Pub. Date: Feb. 22, 2001

Related U.S. Application Data

(60) Provisional application No. 60/149,956, filed on Aug. 18, 1999.

(51) Int. Cl.
*A01N 37/18* (2006.01)
*A61K 38/00* (2006.01)

(52) U.S. Cl. ............................. 514/2; 514/15; 530/300
(58) Field of Classification Search ...................... None
See application file for complete search history.

(56) References Cited

U.S. PATENT DOCUMENTS

| 4,587,046 A * | 5/1986 | Goodman et al. ........... 530/330 |
| 5,767,240 A | 6/1998 | Brenneman et al. |
| 6,174,862 B1 * | 1/2001 | Brenneman .................. 514/15 |
| 6,613,740 B1 | 9/2003 | Gozes et al. |
| 6,933,277 B2 | 8/2005 | Brenneman et al. |
| 2004/0048801 A1 | 3/2004 | Spong et al. |
| 2004/0053313 A1 | 3/2004 | Gozes et al. |

FOREIGN PATENT DOCUMENTS

| EP | 1 206 489 B1 | 5/2004 |
| WO | 92/18140 A1 | 10/1992 |
| WO | 96/11948 A1 | 4/1998 |
| WO | 98/35042 A1 | 8/1998 |
| WO | 00/27875 A2 | 5/2000 |
| WO | 00/53217 A2 | 9/2000 |
| WO | 01/12654 A2 | 2/2001 |

OTHER PUBLICATIONS

Voet et al. (1995). Biochemistry, 2nd Ed. p. 67.*
Rozhavsikaya-arena et al (2000). Endocrinology. 141, 2501-2507.*
saphire et al (1998) JBC. 273, 29764-29769.*
Briggs et al (1996). Gycobiology. 6, 831-836.*
Kuczer et al (1996). Int. J. Protein Res. 48, 286-291.*
Siemon et al (1994) Arcgbh. Immunol Ther. Exp (warsaw). 42, 205-207 (abstract only).*
Bassan, M. et al. "VIP-Induced Mechanism of Neuroprotection: The Complete Sequence of a Femtomolar-Acting Activity-Dependent Neuroprotective Protein." *Regulatory Peptides*, vol. 71, No. 2, (Aug. 15, 1997).
Bassan, M. et al. "Complete Sequence of a Novel Protein Containing a Femtomolar-Activity-Dependent Neuroprotective Peptide." *Journal of Neurochemistry*, vol. 72, pp. 1283-1293 (1999).
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. *Abstracts*, vol. 23, Part 1, p. 1043 (1998).
Brenneman, D.C. and Gozes, I. "A Femtomolar-Acting Neuroprotective Peptide." *Journal of Clinical Investigation*, vol. 97, pp. 2299-2307 (1996).
Brenneman et al. "Neuronal Cell Killing by the Envelope Protein of HIV and Its Prevention by Vasoactive Intestinal Peptide." *Nature* 335:636 (1988).
Brenneman et al. "N-Methyl-D-Aspartate Receptors Influence Neuronal Survival in Developing Spinal Cord Cultures" *Dev. Brain Res.* 51:63 (1990).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. *Abstracts*, vol. 23, Part 2, p. 2250 (1997).
Brenneman, D.E. et al. "Activity-Dependent Neurotrophic Factor: Structure-Activity Relationships of Femtomolar-Acting Peptides." *Journal of Pharmacology and Experimental Therapeutics*, vol. 285, pp. 619-627 (1998).
Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. *Abstracts*, vol. 23, Part 2, p. 2250 (1997).
Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation*, vol. 99. pp. 28377-2841 (1997).

(Continued)

*Primary Examiner*—David Romeo
*Assistant Examiner*—Steven Standley
(74) *Attorney, Agent, or Firm*—Townsend and Townsend and Crew LLP

(57) ABSTRACT

This invention provides an ADNF polypeptide comprising an active core site, the active core site comprising at least one D-amino acid. The invention also provides a pharmaceutical composition comprising an ADNF polypeptide comprising an active core site, the active core site comprising at least one D-amino acid. In particular, the pharmaceutical composition of the invention is orally active. The invention further provides methods for reducing neuronal cell death, methods for reducing oxidative stress, and methods for reducing a condition associated with fetal alcohol syndrome using the ADNF polypeptides and the pharmaceutical compositions of the invention.

12 Claims, 21 Drawing Sheets

OTHER PUBLICATIONS

GenBank Accession No. AB018327 from the DNA Data Bank of Japan (DDBJ) (released Nov. 17, 1998).

Giladi, E. "Protection Against Developmental and Learning Impairments in Apolipoprotein E-Deficient Mice by Activity-Dependent Femtomolar-Acting Peptides." *Neuroscience Letters,* Supplement 48 S1-S80, p. S19 (1997).

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, 27th Annual Meeting, New Orleans, LA, Oct. 25-30, 1997. *Abstracts,* vol. 23, Part 2, p. 2249 (1997).

Glazner, G.W. et al. "Activity Dependent Neurotrophic Factor: A Potent Regulator of Embryonic Growth." *Anat. Embryol.* 200:65-71 (1999).

Gozes, I. and Brenneman, D.E. "Activity-Dependent Neurotrophic Factor (ADNF)." *Journal of Molecular Neuroscience,* vol. 7, pp. 235-244 (1996).

Gozes, I. et al. "Stearyl-Norteucine-Vasoactive Intestinal Peptide (VIP): A novel VIP Analog for Noninvasive Impotence Treatment." *Endocrinology,* vol. 134, p. 2125 (1994).

Gozes, I. et al. "Superactive Lipophilic Peptides Discriminate Multiple Vasoactive Intestinal Peptide Receptors," *Journal of Pharmacology and Experimental Therapeutics,* vol. 273, pp. 161-167 (1995).

Gozes, I. et al. "Neuroprotective Strategy for Alzheimer Disease: Intranasal Administration of a Fatty Neuropeptide." *Proc. Natl. Acad. Sci. USA,* vol. 93, pp. 427-432 (1996).

Gozes I. et al. "Antiserum to Activity-Dependent Neurotrophic Factor Produces Neuronal Cell Death in CNS Cultures: Immunological and Biological Specificity." *Developmental Brain Research,* vol. 99, 167-175 (1997).

Gozes, I. et al. A Femtomolar-Acting Activity-Dependent Neuroprotective Protein (ADNP). *Neuroscience Letters,* Supplement 48 S1-S60, p. S21 (1997).

Gozes, I. et al. "Protection Against Developmental Retardation in Apolipoprotein E-Deficient Mice by a Fatty neuropeptide: Implications for Early Treatment of Alzheimer's Disease." *Journal of Neurobiology,* vol. 33, pp. 329-342 (1997).

Gozes, I. et al. "The cDNA Structure of a Novel Femtomolar-Acting Neuroprotective Protein: Activity-Dependent-Neurotrophic Factor III (ADNFIII)." Society for Neuroscience, 27th Annual Meeting, New Orleans, LA, Oct. 25-30, 1997. *Abstracts,*vol. 23, Part 2, p. 2250 (1997).

Gozes, et al., "A Novel Signaling Molecule for Neuropeptide Action: Activity-dependent Neuroprotective Protein"; Annals of the New York Academy of Sciences, 897:125-135 (1999).

Gozes, I. et al. "Activity-dependent neurotrophic factor: Intranasal administration of femtomolar-acting peptides improve performance in a water maze" *Journal of Pharmacology and Experimental Therapeutics,* vol. 293, pp. 1091-1098 (2000).

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol.* 22(1):103-111 (2000).

Hill, J.M. et al. "Learning Impairment in Adult Mice Produced by Early Embryonic Administration of Antiseum to Activity-Dependent Neurotrophic Factor (ADNF). " Society for Neuroscience, 27th Annual Meeting, New Orleans, LA, Oct. 25-30, 1997. *Abstracts,* vol. 23, Part 2, p. 2250 (1997).

Lilling, G. et al. "Inhibition of Human Neuroblastoma Growth by a Specific VIP Antagonist." *Journal of Molecular Neuroscience,* vol. 5, pp. 231-239 (1995).

Mahato et al. "Development of Targeted Delivery Systems for Nucleic Acid Drugs." *J. of Drug Targeting* 4(6):337-357 (1997) [Abstract].

McKune, S.K. et al. "Localization of mRNA for Activity-Dependent Neurotropic Factor III (ADNF III) in mouse Embryo and Adult CNS." Society for Neuroscience, 27th Annual Meeting, New Orleans, LA, Oct. 25-30, 1997. *Abstracts,* vol. 23, Part 2, p. 2249 (1997).

Nagase, et al., "Prediction of the Coding Sequences of Unidentified Human Genes. XI. The Complete Sequences of 100 New cDNA Clones from Brain Which Code for Large Proteins in vitro"; DNA Research 5:5:277-286 (1998).

Nelbock, P. et al. A cDNA for a Protein that Interacts with the Human Immunodeficiency Virus Tat Transactivator. *Science,* vol. 248, pp. 1650-1653 (1990).

Oberdoester, J. et al. "The Effects of Ethanol on Neuronal Cell Death: Implication for the Fetal Alcohol Syndrome." *FASEB Journal* 12(4):A134 (Mar. 17, 1998).

Pelsman, A. et al. "In Vitro Degeneration of Down Syndrome neurons is Prevented by Activity-Dependent Neurotrophic Factor-Derived Peptides." Society for Neuroscience, 28TH Annual Meeting, Los Angeles, CA, Nov. 7-12, 1998. *Abstracts,* vol. 24, p. 1044 (1998).

Skolnick, J. and Fetrow, J.S. "From Genes to Protein Structure and Function: Novel Applications of Computational Approaches in the Genomic Era." *Trends in Biotech.* 18(1):34-39 (2000).

Smith, A.E. "Viral Vectors in Gene Therapy." *Ann. Rev.Microbiol.* 49:807-838 (1995) [Abstract].

Spinney, L. "New Peptides Prevent Brain Damage." *Molecular Medicine Today* 5(7):282 (Jul. 1999).

Spong et al. "Prevention of Fetal Alcohol Syndrome by Novel Peptides." *FASEB Journal* 13(5):A881 (Mar. 15, 1991).

Spong et al. "Prevention of Fetal Demise and Growth Restriction in a Mouse Model of Fetal Alcohol Syndrome" *The Journal of Pharmacology and Experimental Therapeutics* 297:774-779 (2001).

Voet et al. *Biochemistry, 2nd Ed..* p. 67.

Wilkemeyer et al. "Differential effects of ethanol antagonism and neuroprotection in peptide fragment NAPVSIPQ prevention of ethanol-induced developmental toxicity" *PNAS* 100:8543-8548 (2003).

* cited by examiner

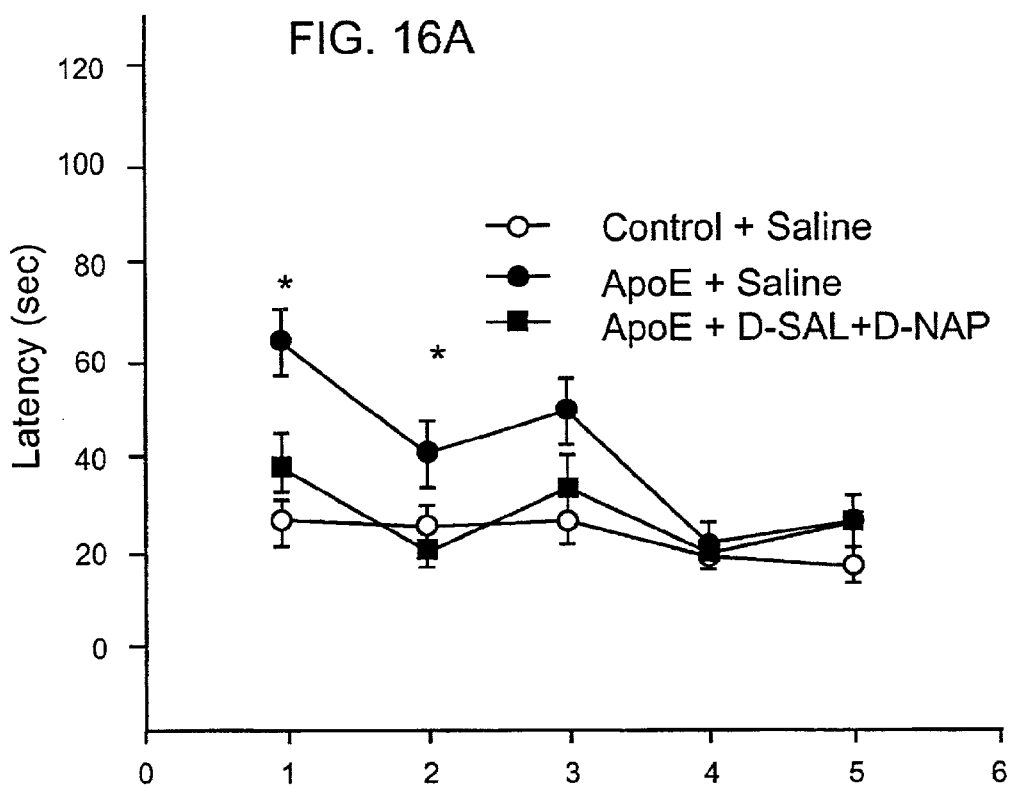
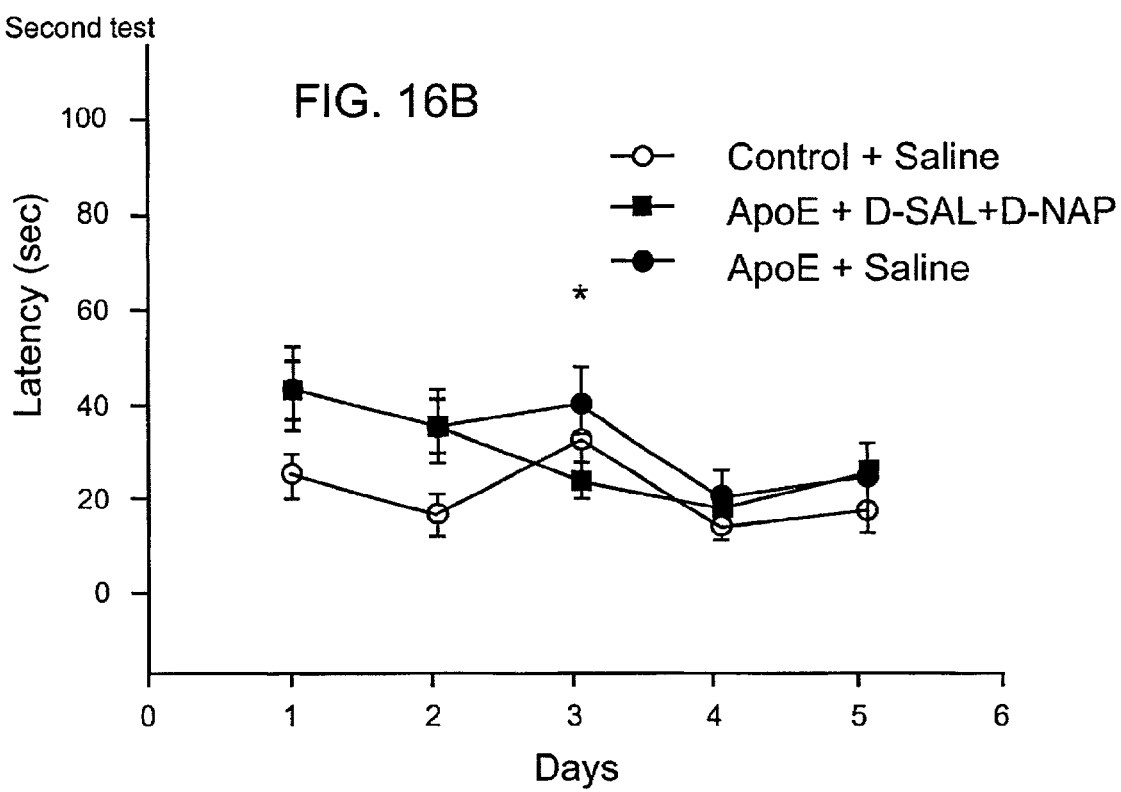

```
                        SEQUENCE LISTING

<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:activity
      dependent neurotrophic factor I (ADNF I) active
      core site, ADNF-9, SAL

<400> SEQUENCE: 1

Ser Ala Leu Leu Arg Ser Ile Pro Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:activity
      dependent neuroprotective protein (ADNP or ADNF
      III) active core site, ADNF III-8, NAP

<400> SEQUENCE: 2

Asn Ala Pro Val Ser Ile Pro Gln
 1               5

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence:ADNF I
      polypeptide
<220> FEATURE:
<221> NAME/KEY: MOD_RES
<222> LOCATION: (1..40)
<223> OTHER INFORMATION: Xaa = any amino acid, Xaa at positions 1-40 may
      be present or absent
```

```
<220> FEATURE:
<221> NAME/KEY: MOD_RES
<222> LOCATION: (50..89)
<223> OTHER INFORMATION: Xaa = any amino acid, Xaa at positions 50-89
      may be present or absent

<400> SEQUENCE: 3

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Ser Ala Leu Leu Arg Ser Ile Pro
             35                  40                  45

Ala Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa
                85

<210> SEQ ID NO 4
<211> LENGTH: 88
<212> TYPE: PRT
<213> ORGANISM: Artificial Sequence
<220> FEATURE:
<223> OTHER INFORMATION: Description of Artificial Sequence:ADNF III
      polypeptide
<220> FEATURE:
<221> NAME/KEY: MOD_RES
<222> LOCATION: (1..40)
<223> OTHER INFORMATION: Xaa = any amino acid, Xaa at positions 1-40 may
      be present or absent
<220> FEATURE:
<221> NAME/KEY: MOD_RES
<222> LOCATION: (49..88)
<223> OTHER INFORMATION: Xaa = any amino acid, Xaa at positions 49-88
      may be present or absent

<400> SEQUENCE: 4

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Asn Ala Pro Val Ser Ile Pro Gln
             35                  40                  45

Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa
                85

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:1-R in
      formula for ADNF I polypeptide

<400> SEQUENCE: 5

Val Leu Gly Gly Gly
 1               5
```

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:1-R in
      formula for ADNF I polypeptide

<400> SEQUENCE: 6

Val Glu Glu Gly Ile Val Leu Gly Gly Gly
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:3-R or 4-R
      in formula for ADNF III polypeptide

<400> SEQUENCE: 7

Leu Gly Leu Gly Gly
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:3-R in
      formula for ADNF III polypeptide

<400> SEQUENCE: 8

Ser Val Arg Leu Gly Leu Gly Gly
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:2-R in
      formula for ADNF I polypeptide

<400> SEQUENCE: 9

Val Leu Gly Gly
 1

<210> SEQ ID NO 10

<400> SEQUENCE: 10

000

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:2-R in
      formula for ADNF I polypeptide

<400> SEQUENCE: 11

Gly Val Leu Gly Gly
 1               5

<210> SEQ ID NO 12
```

```
-continued

<211> LENGTH: 4
<212> TYPE: PRT
<213> ORGANISM: Artificial Sequence
<220> FEATURE:
<223> OTHER INFORMATION: Description of Artificial Sequence:4-R in
      formula for ADNF III polypeptide

<400> SEQUENCE: 12

Leu Gly Leu Gly
  1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:4-R in
      formula for ADNF III polypeptide

<400> SEQUENCE: 13

Val Leu Gly Gly Val
  1               5

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 14

Val Leu Gly Gly Gly Ser Ala Leu Leu Arg Ser Ile Pro Ala
  1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 15

Val Glu Glu Gly Ile Val Leu Gly Gly Gly Ser Ala Leu Leu Arg Ser
  1               5                  10                  15

Ile Pro Ala

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 16

Leu Gly Gly Gly Ser Ala Leu Leu Arg Ser Ile Pro Ala
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:ADNF I
      polypeptide
```

```
<400> SEQUENCE: 17

Gly Gly Gly Ser Ala Leu Leu Arg Ser Ile Pro Ala
  1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 18

Gly Gly Ser Ala Leu Leu Arg Ser Ile Pro Ala
  1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 19

Gly Ser Ala Leu Leu Arg Ser Ile Pro Ala
  1               5                  10
```

ORALLY ACTIVE PEPTIDES THAT PREVENT CELL DAMAGE AND DEATH

CROSS-REFERENCES TO RELATED APPLICATIONS

This application claims benefit of the priority of U.S. provisional application No. 60/149,956, filed Aug. 18, 1999, the disclosure of which is incorporated herein by reference in its entirety. This application is also related to U.S. Ser. No. 07/871,973, filed Apr. 22, 1992, now U.S. Pat. No. 5,767, 240, issued Jun. 16, 1998; U.S. Ser. No. 08/342,297, filed Oct. 17, 1994 (published as WO 96/11948); U.S. Ser. No. 60/037,404, filed Feb. 7, 1997 (published as WO 98/35042); U.S. Ser. No. 09/187,330, filed Nov. 11, 1998; and U.S. Ser. No. 09/267,511, filed Mar. 12, 1999. All of these applications are incorporated herein by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to Activity Dependent Neurotrophic Factor (ADNF) polypeptides comprising at least one D-amino acid within the active core sites of the ADNF polypeptides. The invention also relates to pharmaceutical compositions comprising ADNF polypeptides comprising at least one D-amino acid within the active core sites of the ADNF polypeptides. The invention further relates to methods for reducing neuronal cell death in vitro and in vivo, methods for treating oxidative stress in a patient, and methods for reducing a condition associated with fetal alcohol syndrome in a subject, all of which methods use the ADNF polypeptides of the invention.

BACKGROUND OF THE INVENTION

Neuronal cell death has been associated with various clinical conditions and diseases. These conditions and diseases include, for example, neurodegenerative diseases such as Alzheimer's disease, AIDS-related dementia, Huntington's disease, and Parkinson's disease. Neuronal cell death has been also associated with developmental retardation and learning impairments. These diseases and conditions are severely debilitating and have a lifelong impact on individual's diagnosed with such diseases and conditions.

It has previously been reported that Activity Dependent Neurotrophic Factor (ADNF) polypeptides can be used to prevent or reduce neuronal cell death. Activity Dependent Neurotrophic Factor I (ADNF I) polypeptide is secreted by astroglial cells in the presence of vasoactive intestinal peptide (VIP). The ADNF I polypeptide exhibits survival-promoting activity for neutrons at surprisingly low, femtomolar concentrations (Brenneman & Gozes, *J. Clin. Invest.* 97:2299-2307 (1996)). Further studies identified peptide fragments of ADNF I that mimic the neurotrophic and neuroprotective properties of ADNF I. The shortest peptide (i.e., the active core site) that captured the survival-promoting activity of ADNF I was the peptide SALLRSIPA (SEQ ID NO:1), designated as ADNF-9 or SAL (Brenneman et al., *J. Pharm. Exp. Therp.* 285:619-627 (1998)). Studies of related molecules to the ADNF I polypeptide resulted in the discovery of Activity Dependent Neuroprotective Protein (called ADNP or ADNF III interchangeably). This protein was cloned (Bassan et al., *J. Neurochem.* 72:1283-1293 (1999)) and was found to have an active peptide similar in biological activity to SAL. This peptide (i.e., the active core site) was NAPVSIPQ (SEQ ID NO:2), designated as NAP.

ADNF polypeptides have been shown to prevent neuronal cell death both in vitro and in vivo. For example, ADNF polypeptides have been shown to prevent neuronal cell death associated with tetrodotoxin (electrical blockade), the β-amyloid peptide (the Alzheimer's disease neurotoxin), N-methyl-D-aspartate (excitotoxicity), and the human immune deficiency virus envelope protein. In addition, daily injections of ADNF polypeptides to newborn apolipoprotein-E-deficient mice accelerated the acquisition of developmental reflexes and prevented short-term memory deficits. See, e.g., Bassan et al., *J. Neurochem.* 72:1283-1293 (1999). Moreover, pretreatment with ADNF polypeptides has been previously shown to reduce numerous or various conditions associated with fetal alcohol syndrome in a subject. See, U.S. Ser. No. 09/265,511, filed Mar. 12, 1999.

Although ADNF polypeptides have unlimited potential as neuroprotectants and/or therapeutic agents, it would be advantageous to provide additional ADNF polypeptides that have different properties from the known ADNF polypeptides. For example, availability of a number of ADNF polypeptides with different affinities for their receptors would allow targeting specific receptors in different cell types. Furthermore, additional ADNF polypeptides would aid in designing a drug treatment regime that can be individually tailored for each patient affected by neurodegenerative disorders.

SUMMARY OF THE INVENTION

The present invention is based upon a surprising discovery that ADNF polypeptides comprising D-amino acids, which are not present in nature, are also effective for reducing neuronal cell death, for reducing oxidative stress, for reducing condition(s) associated with fetal alcohol syndrome in a subject, and for other conditions. The ADNF polypeptides include ADNF I and ADNF III polypeptides and subsequences thereof which contain their respective active core sites and provide neuroprotective and growth-promoting functions. The ADNF I polypeptides have an active core site comprising the following amino acid sequence: Ser-Ala-Leu-Leu-Arg-Ser-Ile-Pro-Ala ("SALLR-SIPA" or "SAL"; SEQ ID NO:1). The ADNF III polypeptides also have an active core site comprising a few amino acid residues, namely, the following amino acid sequence: Asn-Ala-Pro-Val-Ser-Ile-Pro-Gln ("NAPVSIPQ" or "NAP"; SEQ ID NO:2). ADNF I polypeptides and ADNF III polypeptides comprising all L-amino acids have been previously shown to have remarkable potency and activity for reducing neuronal cell death in vitro and in vivo, as well as for reducing a condition associated with fetal alcohol syndrome in a subject.

As much, in one aspect, the present invention provides an Activity Dependent Neurotrophic Factor I (ADNF I) comprising an active core site having the following amino acid sequence: Ser-Ala-Leu-Leu-Arg-Ser-Ile-Pro-Ala (SEQ ID NO:1), wherein the active core site comprises at least one D-amino acid. In one embodiment, the N-terminal and/or the C-terminal amino acids of the active core site of the ADNF I polypeptide are D-amino acids. In another embodiment, the active core site of the ADNF I polypeptide comprises all D-amino acids. In another embodiment, an ADNF I polypeptide is Ser-Ala-Leu-Leu-Arg-Ser-Ile-Pro-Ala (SEQ ID NO:1), wherein the ADNF I polypeptide comprises at least one D-amino acid. In another embodiment, the ADNF I polypeptide is Ser-Ala-Leu-Leu-Arg-Ser-Ile-Pro-Ala (SEQ ID NO:1), wherein the ADNF I polypeptide comprises all D-amino acids.

In another aspect, the present invention provides an Activity Dependent Neurotrophic Factor III (ADNF III) comprising an active core site having the following amino acid sequence: Asn-Ala-Pro-Val-Ser-Ile-Pro-Gln (SEQ ID NO:2), wherein the active core site comprises at least one D-amino acid. In one embodiment, the N-terminal and/or the C-terminal amino acids of the active core site are D-amino acids. In another embodiment, the active core site of the ADNF III polypeptide comprises all D-amino acids. In another embodiment, the ADNF III polypeptide is Asn-Ala-Pro-Val-Ser-Ile-Pro-Gln (SEQ ID NO:2), wherein the ADNF III polypeptide comprises at least one D-amino acid. In another embodiment, the ADNF III polypeptide is Asn-Ala-Pro-Val-Ser-Ile-Pro-Gln (SEQ ID NO:2), wherein the ADNF III polypeptide comprises all D-amino acids.

In yet another aspect, the present invention provides a pharmaceutical composition comprising a pharmaceutically acceptable excipient and an ADNF polypeptide, wherein the ADNF polypeptide is a member selected from the group consisting of: (a) an ADNF I polypeptide comprising an active core site having the following amino acid: Ser-Ala-Leu-Leu-Arg-Ser-Ile-Pro-Ala (SEQ ID NO:1); (b) an ADNF III polypeptide comprising an active core site having the following amino acid: Asn-Ala-Pro-Val-Ser-Ile-Pro-Gln (SEQ ID NO:2); and (c) a mixture of the ADNF I polypeptide or part (a) and the ADNF III polypeptide of part (b); wherein at least one of the ADNF I polypeptide and the ADNF III polypeptide comprises an active core site comprising at least one D-amino acid.

In one embodiment, the pharmaceutical composition comprises an ADNF I polypeptide, wherein the ADNF I polypeptide comprises all D-amino acids. In another embodiment, the pharmaceutical composition comprises an ADNF III polypeptide, wherein the ADNF III polypeptide comprises all D-amino acids. In another embodiment, the pharmaceutical composition comprises an ADNF I polypeptide and an ADNF III polypeptide, wherein the ADNF I polypeptide and the ADNF III polypeptide both comprise all D-amino acids. In another embodiment, the pharmaceutical composition comprises an ADNF I polypeptide and an ADNF III polypeptide, wherein the ADNF I peptide comprises all D-amino acids and wherein the ADNF III polypeptide comprises all L-amino acids. In another embodiment, the pharmaceutical composition comprises an ADNF I polypeptide and an ADNF III polypeptide, wherein the ADNF I polypeptide comprises all L-amino acids and wherein the ADNF III polypeptide comprises all D-amino acids.

In yet another aspect, the present invention provides a method for preventing neuronal cell death, the method comprising contacting neuronal cells with at least one of the above described ADNF polypeptides. In one embodiment, the neuronal cell death is in a patient infected with immunodeficiency virus. In another embodiment, the neuronal cell death is associated with excito-toxicity induced by N-methyl-D-aspartate stimulation. In yet another embodiment, the neuronal cell death is induced by the beta-amyloid peptide in a patient afflicted with Alzheimer's disease. In yet another embodiment, the neuronal cell death is induced by cholinergic blockade in a patient afflicted with Alzheimer's disease, which results in learning impairment.

In yet another aspect, the present invention provides a method for reducing oxidative stress in a patient, the method comprising administrating to the patient at least one of the ADNF polypeptides described above in an amount sufficient to treat oxidative stress.

In yet another aspect, the present invention provides a method for reducing a condition associated with fetal alcohol syndrome in a subject who is exposed to alcohol in utero, the method comprising administering to the subject at least one ADNF polypeptides described above in an amount sufficient to reduce a condition associated with fetal alcohol syndrome.

BRIEF DESCRIPTION OF THE DRAWINGS

As shown in FIG. 14A, the time required to reach the platform (indicative of learning and intact reference memory) was measured (first test). After 0.5 minute on the platform, the animal was placed back in the water (in the previous position) for an additional second test (FIG. 14B) and search for the hidden platform (retained in the previous position). The time required to reach the platform in the second trail was recorded, indicative of short-term (working) memory. All measurements were performed using the computerized video-assisted HVS water maze system (HVS Image Ltd. Hampton, UK). Animals were tested for four days to eliminate random memory defective animals. The designated n is the number of animals tested. Each point is the mean+the standard error.

FIGS. 16A and 16B illustrate the first test and second test, respectively, of Morris water maze test results in apolipoprotein E-deficient mice. Experiments were performed following injections of a mixture of D-NAP+D-SAL with an injection protocol and Morris water maze as described in Gozes et al., *J. Pharmacol. Exp. Therap.* 293:1091-1098 (2000). Results showed significant improvements on day 1 and day 2 (first daily test), and on day three (second daily test)—P<0.05.

DEFINITIONS

Figure 1:
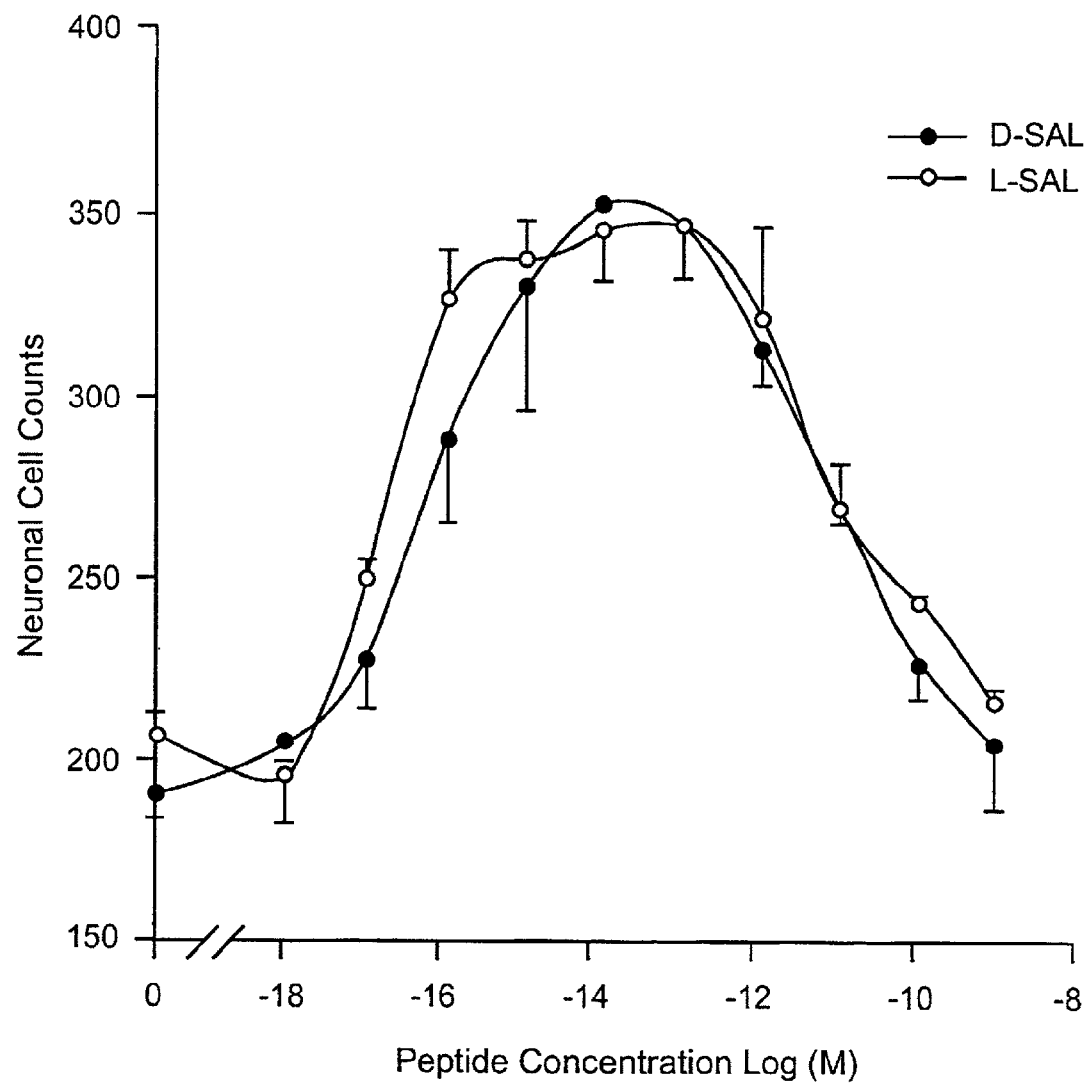
FIG. 1 compares the survival-promoting activity of D- and L-forms of SALLRSIPA (SEQ ID NO:1) in dissociated cerebral cortical cultures treated with 1 μM tetrodotoxin, an agent that blocks electrical activity and produces apoptotic neuronal cell death. Treatment duration was for 5 days. Each point is the mean ± the standard error of 3-4 determinations. Neuronal cell counts were obtained without knowledge of the treatment group.

The phrase "ADNF polypeptide" refers to one or more activity dependent neurotrophic factors (ADNF) that have an active core site comprising the amino acid sequence of SALLRSIPA (SEQ ID NO:1) or NAPVSIPQ (SEQ ID NO:2), or conservatively modified variants thereof that have neurotrophic/neuroprotective activity as measured with in vitro cortical neuron culture assays described by, e.g., Brenneman et al., *J. Pharmacol. Exp. Therp.* 285:629-627 (1998); Bassan et al., *J. Neurochem.* 72:1283-1293 (1999). An ADNF polypeptide can be an ADNF I polypeptide, an ADNF III polypeptide, their alleles, polymorphic variants, or interspecies homolog, or any subsequences thereof, such as NAP and SAL, that exhibit neuroprotective/neurotrophic action on, e.g., neurons originating in the central nervous system either in vitro or in vivo. An "ADNF polypeptide" can also refer to a mixture of ADNF I polypeptide and ADNF III polypeptide.

The term "ADNF I" refers to an activity dependent neurotrophic factor polypeptide having a molecular weight of about 14,000 Daltons with a pI of 8.3±0.25. As described above, ADNF I polypeptides have an active core site comprising an amino acid sequence of Ser-Ala-Leu-Leu-Arg-Ser-Ile-Pro-Ala (also referred to as "SALLRSIPA," "SAL," or "ADNF I-9"; SEQ ID NO:1). See, Brenneman et al., *J. Clin. Invest.* 97:2299-2307 (1996), Glazner et al., *Anat. Embryol.* 200:65-71 (1999), Brenneman et al., *J. Pharm. Exp. Ther.* 285:619-27 (1998), Gozes & Brenneman, *J. Mol. Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu.

The terms "ADNF III" and "ADNP" refer to an activity dependent neurotrophic factor polypeptide having a predicted molecular weight of about 95 kDa (about 828 amino acid residues) and a pI of about 5.99. As described above, ADNF III polypeptides have an active core site comprising an amino acid sequence of Asn-Ala-Pro-Val-Ser-Ile-Pro-Gln (also referred to as "NAPVSIPQ," "NAP," or "ADNF III-8"; SEQ ID NO:2). See, Bassan et al., *J. Neurochem.* 72:1283-1293 (1999), incorporated herein by reference. Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro.

The phrase "reducing neuronal cell death" refers to reduction, including prevention, of neuronal cell death. Reduction is a change of a parameter by about 10% to about 100%, preferably at least about 50%, and more preferably at least about 80% compared to that of the control (e.g., without treatment with, e.g., ADNF polypeptides). The reduction of neuronal cell death can be measured by any methods known in the art. For example, ADNF polypeptides that reduce neuronal cell death can be screened using the various methods described in U.S. Ser. No. 60/037,404, filed Feb. 27, 1997 (published as WO 98/35042) and U.S. Ser. No. 09/187,330, filed Nov. 6, 1998, both of which are incorporated herein by reference.

The phrase "oxidative stress" in cells or tissues refers to enhanced generation of free radicals or reactive oxygen species (ROS) (such as α-hydroxy ethyl radical, superoxide radical, hydroxy radical, peroxy radical, and hydrogen peroxide) and/or a depletion in antioxidant defense system causing an imbalance between prooxidants and antioxidants. Enzymatic antioxidant system includes, e.g., superoxide dismutase, catalase, glutathione perixidase, and glutathione reductase, and nonenzymatic antioxidants include, e.g., reduced glutathione, vitamin A, C, and E. See, Schlorff et al., *Alcohol* 17:97-105 (1999).

The phrase "reducing oxidative stress" refers to reduction, including prevention, of oxidative stress in cells and tissues. Reduction is a change of a parameter by about 10% to about 100%, preferably at least about 50%, and more preferably at least about 80% compared to that of the control (e.g., without treatment with, e.g., ADNF polypeptides). The reduction in oxidative stress can be measured by any methods known in the art. For example, ADNF polypeptides that reduce oxidative stress can be screened by using primary neurons treated with $FeSO_4$ in vitro as described infra. Also, ADNF polypeptides that reduce oxidative stress can be screened using animals that ingested ethanol which is known to cause oxidative stress in cells and tissues. For example, the effects of ADNF polypeptides on lipid peroxidation in plasma and/or antioxidant system of rats that ingested ethanol can be used. See, e.g., Schlorff et al., *Alcohol* 17:97-105 (1999).

The phrases "fetal alcohol syndrome" and "fetal alcohol effects" relate to various physical and mental conditions of an embryo, a fetus, or a subject who is exposed to alcohol in utero (e.g. whose mother consumed alcohol during pregnancy) in an amount sufficient to initiate the development of these conditions or to cause these conditions in the absence of prevention treatment, e.g., treatment with ADNF polypeptides. Some of these conditions include, but are not limited to, the following:

skeletal deformities: deformed ribs and sternum; curved spine; hip dislocations; bent, fused, webbed, or missing fingers or toes; limited movement of joints; small head; facial abnormalities: small eye openings; skin webbing between eyes and base of nose; drooping eyelids; nearsightedness; failure of eyes to move in same direction; short upturned nose; sunken nasal bridge; flat or absent groove between nose and upper lip; thin upper lip; opening in roof of mouth; small jaw; low-set or poorly formed ears; organ deformities: heart defects; heart murmurs; genital malformations; kidney and urinary defects; central nervous system handicaps: small brain; faulty arrangement of brain cells and connective tissue; mental retardation—usually mild to moderate, but occasionally severe; learning disabilities; short attention span; irritability in infancy; hyperactivity in childhood; poor body, hand, and finger coordination (see, e.g., www.well.com/user/woa/fsfas.htm); and other abnormalities: brain weight reduction, body weight reduction, a higher rate of death in utero, and a decrease in the level of VIP (e.g., VIP mRNA).

The phrase "reducing a condition associated with fetal alcohol syndrome" refers to reduction, including prevention, of parameters associated with fetal alcohol syndrome. Reduction is a change of a parameter by about 10% to about 100%, preferably at least about 50%, and more preferably at least about 80% compared to that of the control (e.g., exposed to alcohol in utero without any treatment, e.g., treatment with ADNF polypeptides). The parameters can be any physical or mental condition listed above. For example, they can be: (1) the percentage of fetus death, (2) fetal weights and fetal brain weights, (3) the level of VIP (e.g., VIP mRNA) in embryos, (4) learning and/or memory, and (5) the glutathione level.

The phrase "a subject with fetal alcohol syndrome" relates to an embryo, a fetus, or a subject, in particular a human, who is exposed to alcohol in utero and who has fetal alcohol syndrome or who is at risk or in danger of developing, due to maternal alcohol consumption, any of the conditions related to fetal alcohol syndrome, such as the effects described above.

The term "memory" includes all medical classifications of memory, e.g., sensory, immediate, recent and remote, as well as terms used in psychology, such as reference memory, which refers to information gained from previous experience, either recent or remote (see, e.g., *Harrison's Principles of Internal Medicine,* volume 1, pp. 142-150 (Fauci et al., eds., 1988)).

Various parameters can be measured to determine if an ADNF polypeptide or a mixture of ADNF polypeptides improves performance of a subject (e.g., learning and memory). For example, the degree of learning deficits can be compared between the control (e.g., untreated with ADNF polypeptides) and a group pretreated with ADNF polypeptides. The phrase "improving learning and memory" refers to an improvement or enhancement of at least one parameter that indicates learning and memory. Improvement or enhancement is change of a parameter by at least 10%, optionally at least about 20%, at least about 30%, at least about 40%, at least about 50%, at least about 60%, at least about 70%, at least about 80%, at least about 90%, at least about 100%, at least about 150%, at least about 200%, etc. The improvement of learning and memory can be measured by any methods known in the art. For example, ADNF polypeptides that improve learning and memory can be screened using Morris water maze (see, e.g., the materials and methods section). See, also, Gozes et al., *Proc. Natl. Acad. Sci. USA* 93:427-432 (1996); Gozes et al., *J. Pharmacol. Exp. Therap.* 293:1091-1098 (2000).

The term "contacting" is used herein interchangeably with the following: combined with, added to, mixed with, passed over, incubated with, flowed over, etc. Moreover, the ADNF polypeptides of the present invention can be "administered" by any conventional method such as, for example, parenteral, oral, topical, and inhalation routes. In preferred embodiments, oral administration is employed. In the context of methods related to fetal alcohol syndrome, ADNF polypeptides can be administered directly to an embryo, a fetus, or a subject in utero or to the subject in utero indirectly, by administering the polypeptide to the mother by any other methods described herein.

"An amount sufficient" or "an effective amount" is that amount of a given ADNF polypeptide that reduces neuronal cell death or reduces fetal alcohol syndrome or oxidative stress as described herein. For example, in the context of neuronal death, "an amount sufficient" or "an effective amount" is that amount of a given ADNF polypeptide that reduces neuronal cell death in the assays of, e.g., Hill et al., *Brain Res.* 603:222-233 (1993); Brenneman et al., *Nature* 335:639-642 (1988); or Brenneman et al., *Dev. Brain Res.* 51:63-68 (1990); Forsythe & Westbrook, *J. Physiol. Lond.* 396:515-533 (1988). In the context of reducing oxidative stress, "an amount sufficient" or "an effective amount" is that amount of ADNF polypeptide that reduces or prevents, e.g., changes in lipid peroxidation in plasma or changes in antioxidant system in accordance with the assays described in Schlorff et al., *Alcohol* 17:97-105 (1999). In the context of reducing fetal alcohol syndrome, "an amount sufficient" or "an effective amount" is that amount of a given ADNF polypeptide that reduces or prevents, for example, (1) the percentage of fetus death, (2) a reduction in fetal weights and fetal brain weights, or (3) a reduction in the level of VIP mRNA in embryos. The dosing range can vary depending on the ADNF polypeptide used, the route of administration and the potency of the particular ADNF polypeptide, but can readily be determined using the foregoing assays.

The term "biologically active" refers to a peptide sequence that will interact with naturally occurring biological molecules to either activate or inhibit the function of those molecules in vitro or in vivo. The term "biologically active" is most commonly used herein to refer to ADNF polypeptides or subsequences thereof that exhibit neuroprotective/neurotrophic action on neurons originating in the central nervous system either in vitro or in vivo. The neuroprotective/neurotrophic action of ADNF polypeptides can be tested using, e.g., cerebral cortical cultures treated with a neurotoxin (see, Gozes et al., *Proc. Nat'l. Acad. Sci. USA* 93:427-432 (1996)).

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF nucleic acid is separated from open reading frames that flank the ADNF gene and encode proteins other than ADNF. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The term "amino acid" refers to naturally occurring amino acids in L-form and their enantiomers in D-form, amino acid analogs, and amino acid mimetics. The two-mirror-image forms (enantiomers) of amino acids are called the L-isomer and the D-isomer, where L refers to levorotatory (left rotation of the plane of polarization of light) and D refers to dextrorotatory (right rotation of the plane of polarization). The term "amino acid" also includes amino acids that are later modified, e.g., hydroxyproline, γ-carboxyglutatmate, and O-phosphoserine. Amino acid analogs refer to synthetic amino acids that have the same basic chemical structure as naturally occurring amino acids in L-form or their enantiomers in D-form, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acid analogs and amino acids mimetics can also be in L-form or in D-form.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

(see, e.g., Creighton, *Proteins* (1984)).

The terms "polypeptide," "peptide," and "protein" are used interchangeably herein to refer to a polymer of amino acid residues. The terms apply to amino acid polymers in which one or more amino acid residue is a naturally occurring amino acid in L-form or their enantiomers in D-form, an analog or mimetic of amino acids in L-form or D-form, or combinations thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=4 and a comparison of both strands. For amino acid sequences, the BLASTP program uses as defaults a wordlength of 3, and expectation (E) of 10, and the BLOSUM62 scoring matrix (see Henikoff & Henikoff, *Prac. Natl. Acad. Sci. USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Nat'l Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$ 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5×

SSC, 1% SDS, incubating at 65° C., with a wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency.

DETAILED DESCRIPTION OF THE INVENTION AND PREFERRED EMBODIMENTS

I. Introduction

The chirality (left or right handedness) of a peptide pertains to the tetrahedral array of four different groups about the α-carbon atom of the constituent amino acids that confers optical activity. The two-mirror-image forms (enantiomers) of amino acids are called the L-isomer and the D-isomer, where L refers to levorotatory (left rotation of the plane of polarization of light) and D refers to dextrorotatory (right rotation of the plane of polarization). Only L-amino acids are constituents of naturally occurring proteins. Classical receptor pharmacology teaches that membrane receptors readily discriminate between L- and D-agonists and antagonists. Receptor activation is mediated through a stereoselective preference for agents in the naturally occurring L-isomer form.

Because ADNF I and ADNF III polypeptides are neurotrophic factors, it was predicted that ADNF I and ADNF III polypeptides comprising D-amino acids would not be able to activate their respective stereoselective membrane receptors. Surprisingly, it was found that ADNF I and ADNF III polypeptides comprising D-amino acids were bioactive. In fact, all D- and all L-amino acid forms of the active core site peptide from ADNF I polypeptides, i.e., SALLRSIPA (SEQ ID NO:1) (SAL), were virtually identical in neuronal survival activity in vitro. Similarly, all D- and all L-amino acid forms of the active core site peptide from ADNF III polypeptides, i.e., NAPVSIPQ (SEQ ID NO:2) (NAP), were virtually identical in neuronal survival activity in vitro. It is very uncommon that all D-amino acid peptides are active, and even more uncommon that the D- and L-isomers of a given peptide are equally active.

A few examples of peptides with similar actions in D- vs. L-forms have been reported. A well-known example is beta amyloid. It was shown that bioactivity of D-isomers of beta amyloid 1-42 is identical to that observed with the L-form of the peptide (Cribbs et al., *J. Biol. Chem.* 272:7431-7436 (1997)). Another example is the immunosuppressive effects of D- and L-peptides derived from the HLA class I heavy chain (Woo et al., *Transplantation* 64:1460-1467 (1997)). Although these examples illustrate that bioactivity of peptides can be non-stereoselective, this phenomenon is very rare. This is because biological macromolecules are made up of monomer molecules of uniform chirality (Mason, *Chirality* 3:223 (1990)) and the biochemical interactions of biological macromolecules are inherently chiral. In fact, for neurotrophic agents, there is no known example that exhibits non-chiral properties. Thus, it is surprising that ADNF polypeptides of the present invention provide neuroprotection through a non-chiral mechanism.

The fact that ADNF polypeptides comprising D-amino acids are bioactive allows these polypeptides to be administered orally. Compared to L-isomers, D-isomers of peptides have increased stability in the gastrointestinal tract and can be absorbed without change (He et al., *J. Pharmaceutical Sci.* 87:626-633 (1998)). For example, in He et al., bioavailability (as measured by the appearance of unchanged labeled D-peptides in the urine after 24-48 hours) was estimated at 13% with compounds of molecular mass of 900 Daltons, the approximate size of the active core sites of ADNF I and ADNF III polypeptides. ADNF polypeptides comprising D-amino acids provide a longer bioavailability, and thus can be formulated for oral administration.

As such, the present invention provides for the first time, inter alia, ADNF polypeptides comprising at least one D-amino acid within their active core sites, preferably at the N-terminus and/or the C-terminus of the active core sites. In a presently preferred embodiment, the invention provides ADNF polypeptides comprising all D-amino acids. The invention also provides a pharmaceutical composition comprising a pharmaceutically acceptable excipient and an ADNF I polypeptide, an ADNF III polypeptide, or a mixture thereof, wherein at least one of the ADNF I polypeptide or the ADNF III polypeptide comprises at least one D-amino acid within its active core site. In particular, the invention provides an orally active pharmaceutical composition comprising an ADNF polypeptide comprising at least one D-amino acid within its active core site. The ADNF polypeptides and the pharmaceutical compositions of the present invention can be used, inter alia, in methods for reducing neuronal cell death, for reducing oxidative stress in a patient, and for reducing a condition associated with fetal alcohol syndrome.

II. ADNF Polypeptides Comprising D-amino Acids and Methods of Making the Polypeptides In one aspect, the present invention provides an ADNF polypeptide comprising at least one D-amino acid within its active core site, preferably at the N-terminus and/or the C-terminus of the active core site. Since D-enantiomers of polypeptides are enzymatically more stable than their L-enantiomers, an ADNF polypeptide comprising D-amino acids provides a longer bioavailability compared to its counterpart comprising L-amino acids. In particular, the ADNF polypeptides comprising D-amino acids are stable in the gastrointestinal tract and can be absorbed without cleavage in the human body. Therefore, the ADNF polypeptides of the present invention are particularly useful as an oral agent.

In one embodiment, the ADNF I polypeptide comprises an active core site having the following amino acid sequence: Ser-Ala-Leu-Arg-Ser-Ile-Pro-Ala (SEQ ID NO:1), wherein the active core site comprises at least one D-amino acid. In another embodiment, both the N-terminal and/or the C-terminal amino acids of the active core site of the ADNF I polypeptide are D-amino acids. In yet another embodiment, the active core site of the ADNF I polypeptide comprises D-amino acids at locations other than at the N-terminus and/or the C-terminus of the active core site. For example, any amino acids within the active core site can be a D-amino acid. In other words, any one or any combinations of serine, alanine, leucine, leucine, arginine, serine, isoleucine, proline, and alanine within the active core site of the ADNF I polypeptides can be a D-amino acid. For instance, every other amino acid within the active core site of the ADNF I polypeptide can be a D-amino acid. In a preferred embodiment, the active core site of the ADNF I polypeptide comprises all D-amino acids.

In yet another embodiment, the ADNF I polypeptide can comprise additional amino acids at the N-terminua and/or at the C-terminus of the active core site. For example, the ADNF I polypeptide can comprise up to 40 amino acids at the N-terminus and/or the C-terminus of the active core site. In another example, the ADNF I polypeptide can comprise up to 20 amino acids at the N-terminus and/or the C-terminus of the active core site. In yet another example, the ADNF I polypeptide can comprise up to 10 amino acids at the N-terminus and/or the C-terminus of the active core site. In these embodiments, preferably the N-terminal amino acid and/or the C-terminal amino acid of the ADNF I polypeptide are D-amino acids. Any one of the additional amino acids or all of the additional amino acids can be D-amino acids. In a preferred embodiment, the ADNF I polypeptide does not comprise any additional amino acids and has an amino acid sequence of Ser-Ala-Leu-Leu-Arg-Ser-Ile-Pro-Ala (SEQ ID NO:1), wherein the ADNF I polypeptide comprises all D-amino acids.

In another embodiment, the ADNF III polypeptide comprises an active core site having the following amino acid sequence: Asn-Ala-Pro-Val-Ser-Ile-Pro-Gln (SEQ ID NO:2), wherein the active core site comprises at least one D-amino acid. In another embodiment, both the N-terminal and/or C-terminal amino acids of the active core site of the ADNF III polypeptide are D-amino acids. In yet another embodiment, the active-core site of the ADNF III polypeptide comprises D-amino acids at locations other than at the N- or C-terminus of the active core site. For example, any amino acids within the active core site can be a D-amino acid. In other words, any one or any combination of asparagine, alanine, proline, valine, serine, isoleucine, proline, and glutamine within the active core site of the ADNF III polypeptides can be a D-amino acid. For instance, every other amino acid within the active core site of the ADNF III polypeptide can be a D-amino acid. In a preferred embodiment, the active core site of the ADNF III polypeptide comprises all D-amino acids.

In yet another embodiment, the ADNF III polypeptide can comprise additional amino acids at the N-terminus and/or at the C-terminus of the active core site. For example, the ADNF III polypeptide can comprise up to 40 amino acids at the N-terminus and/or the C-terminus of the active core site. In another example, the ADNF III polypeptide can comprise up to 20 amino acids at the N-terminus and/or the C-terminus of the active core site. In yet another example, the ADNF III polypeptide can comprise up to 10 amino acids at the N-terminus and/or the C-terminus of the active core site. In these embodiments, preferably the N-terminal amino acid and/or the C-terminal amino acid of the ADNF I polypeptide are D-amino acids. Any one of the additional amino acids or all of the additional amino acids can be D-amino acids. In a preferred embodiment, the ADNF III polypeptide does not comprise any additional amino acids and has an amino acid sequence of Asn-Ala-Pro-Val-Ser-Ile-Pro-Gln (SEQ ID NO:2), wherein the ADNF III polypeptide comprises all D-amino acids.

In a preferred embodiment, the ADNF I polypeptide comprises an amino acid sequence having the following formula: $(R^1)_x$-Ser-Ala-Leu-Leu-Arg-Ser-Ile-Pro-Ala-$(R^2)_y$ (SEQ ID NO:3), wherein the active core site comprises at least one D-amino acid. In another preferred embodiment, the ADNF III polypeptide comprises an amino acid sequence having the following formula: $(R_3)_w$-Asn-Ala-Pro-Val-Ser-Ile-Pro-Gln-$(R^4)_z$ (SEQ ID NO:4), wherein the active core site comprises at least one D-amino acid. In these preferred embodiments, the previous discussion pertaining to the location and the number of D-amino acids within the active core sites of the ADNF I and ADNF III polypeptides is fully applicable, and thus, will not be repeated with respect to these particular embodiments of the invention.

In the above formula, each of $R^1$, $R^2$, $R^3$, and $R^4$, if present, is an amino acid sequence comprising from 1 to about 40 amino acids wherein each amino acid in the amino acid sequence is independently selected. The term "independently selected" is used herein to indicate that the amino acids making up, for example, the amino acid sequence $R^1$ may be identical or different (e.g., all of the amino acids in the amino acid sequence may be threonine, etc.). This discussion pertaining to $R^1$ is fully applicable to $R^2$, $R^3$, and $R^4$. Moreover, any one or any combinations of the amino acids making up the amino acid sequence $R^1$ can be a D-amino acid or an L-amino acid. In one embodiment, the N-terminal amino acid of $R^1$ is a D-amino acid and/or the C-terminal amino acid of $R^2$ is a D-amino acid. In another embodiment, the N-terminal amino acid of $R^3$ is a D-amino acid and/or the C-terminal amino acid of $R^4$ is a D-amino acid. In another embodiment, each of $R^1$, $R^2$, $R^3$, and $R^4$ comprises all D-amino acids.

Within the above formula for the ADNF I polypeptide, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero. Moreover, if x and y are both one, the amino acid sequences $R^1$ and $R^2$ may be the same or different. As such, the amino acid sequences $R^1$ and $R^2$ are independently selected. If $R^1$ and $R^2$ are the same, they are identical in terms of both chain length and amino acid composition. For example, both $R^1$ and $R^2$ may be Val-Leu-Gly-Gly-Gly (SEQ ID NO:5). If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:5), whereas $R^2$ may be Val-Leu-Gly-Gly (SEQ ID NO:9). Alternatively, $R^1$ may be Val-Leu-Gly-Gly-Gly (SEQ ID NO:5), whereas $R^2$ may be Val-Leu-Gly-Gly-Val (SEQ ID NO:13). Alternatively, $R^1$ may be Val-Leu-Gly-Gly-Gly (SEQ ID NO:5), whereas $R^2$ may be Gly-Val-Leu-Gly-Gly (SEQ ID NO:11).

Similarly, w and z are independently selected and are equal to zero or one within the above formula for the ADNF III polypeptide. The term independently selected is used herein to indicate that w and z may be identical or different. For example, w and z may both be zero or, alternatively, w and z may both be one. In addition, w may be zero and z may be one or, alternatively, w may be one and z may be zero. Moreover, if w and z are both one, the amino acid sequences $R^3$ and $R^4$ may be the same or different. As such, the amino acid sequences $R^3$ and $R^4$ are independently selected. If $R^3$ and $R^4$ are the same, they are identical in terms of both chain length and amino acid composition. For example, both $R^3$ and $R^4$ may be Leu-Gly-Leu-Gly-Gly (SEQ ID NO:7). If $R^3$ and $R^4$ are different, they can differ from one another in terms of chain length and/or amino acid composition and/or order of amino acids in the amino acids sequences. For example, $R^3$ may be Leu-Gly-Leu-Gly-Gly (SEQ ID NO:7), whereas R⁴ may be Leu-Gly-Leu-Gly (SEQ ID NO:12). Alternatively, R³ may be Leu-Gly-Leu-Gly-Gly (SEQ ID NO:7), whereas R⁴ may be Leu-Gly-Leu-Gly-Leu (SEQ ID NO:13).

Within the scope, certain ADNF I and ADNF III polypeptides are preferred, namely those in which x, y, w, and z are all zero (i.e., SALLRSIPA (SEQ ID NO:1) and NAPVSIPQ (SEQ ID NO:2), respectively). Equally preferred are ADNF I polypeptides in which x is one; R¹ is Val-Leu-Gly-Gly-Gly (SEQ ID NO:5); and y is zero. Also equally preferred are ADNF I polypeptides in which x is one; R¹ is Val-Glu-Glu-Gly-Ile-Val-Leu-Gly-Gly-Gly (SEQ ID NO:6); and y is zero. Also equally preferred are ADNF III polypeptides in which w is one; R³ is Gly-Gly; and z is zero. Also equally preferred are ADNF III polypeptides in which w is one; R³ is Leu-Glu-Gly; z is one; and R⁴ is Gln-Ser. Also equally preferred are ADNF III polypeptides in which w is one; R³ is Leu-Gly-Leu-Gly-Gly- (SEQ ID NO:7); z is one; and R⁴ is Gln-Ser. Also equally preferred are ADNF III polypeptides in which w is one; R³ is Ser-Val-Arg-Leu-Gly-Leu-Gly-Gly (SEQ ID NO:8); z is one; and R⁴ is Gln-Ser. Additional amino acids can be added to both the N-terminus and the C-terminus of these active core sites (SALLRSIPA (SEQ ID NO:1) or NAPVSIPO (SEQ ID NO:2)) without loss of biological activity as evidenced by the fact that the intact ADNF I or ADNF III growth factors exhibit extraordinary biological activity. See, U.S. Ser. No. 08/324,297, filed Oct. 17, 1994 (also published as WO 96/11948) for the description of ADNF I polypeptides; and U.S. Ser. No. 60/037,404 filed Feb. 27, 1997 and U.S. Ser. No. 60/059,621 filed, Sep. 23, 1997 (also published as WO 98/35042) for the description of ADNF III polypeptides, all of which are incorporated herein by reference.

The ADNF polypeptides comprising at least one D-amino acid within the active core sites of the ADNF polypeptides can be prepared via a wide variety of well-known techniques. Polypeptides of relatively short size are typically synthesized in solution or on a solid support in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Using solid phase synthesis methods, one or more D-amino acids can be inserted, instead of L-amino acids, into an ADNF polypeptide at any desired location(s). Techniques for solid phase synthesis are described by Barany & Merrifield, *Solid-Phase Peptide Synthesis;* pp. 3-284 in *The Peptides: Analysis, Synthesis, Biology.* Vol. 2: *Special Methods in Peptide Synthesis,* Part A.; Merrifield et al., *J. Am. Chem. Soc.* 85:2149-2156 (1963); and Stewart et al., *Solid Phase Peptide Synthesis* (2nd ed. 1984).

Alternatively, ADNF polypeptides comprising at least one D-amino acid within their active core sites can be synthesized using both recombinant DNA methods and chemical synthesis. For example, fragments of an ADNF polypeptide comprising D-amino acids can be chemically synthesized using solid phase synthesis methods described above, and fragments of an ADNF polypeptide comprising L-amino acids can be produced recombinantly. That is, expression vectors containing a nucleic acid encoding a fragment of an ADNF polypeptide can be introduced into host cells, and then the expressed ADNF polypeptide fragments can be purified. These ADNF polypeptide fragments comprising D-amino acids and ADNF polypeptide fragments comprising L-amino acids can then be chemically linked to one another.

After chemical synthesis, biological expression or purification, the polypeptide(s) may possess a conformation substantially different than the native conformations of the constituents polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will appreciate that many conservative variations of the ADNF polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

Moreover, one of skill will recognize that other modifications can also be made to the ADNF polypeptides comprising at least one D-amino acid without diminishing their biological activity. For example, modifications can be made to avoid cleavage by enzymes in the stomach or intestines. In another example, modifications can be made to aid the purification process.

It will be readily apparent to those of ordinary skill in the art that the biologically active ADNF polypeptides of the present invention can readily be screened for neuroprotective/neurotrophic activity using a number of methods known in the art. For example, a cerebral cortical cell culture assay can be used. In cerebral cortical cell culture assays, cerebral cortical cell cultures are prepared using the techniques described by Forsythe & Westbrook, *J. Physiol. Lond.* 396:515-533 (1988) with the following modifications. Cerebral cortex are used instead of hippocampus, and newborn rats are used instead of E16 mice. After nine days growth in vitro, the cultures are given a complete change of medium and treated with the ADNF polypeptide of interest (dissolved in phosphate buffered saline) for an additional five days. To terminate, the cells are fixed for immunocytochemistry and neurons identified with antibodies against NSE (i.e., neuron specific enolase, a neuronal specific marker). Cell counts are performed on 30 fields, with total area of about 15 mm². Neurons are counted without knowledge of treatment. Control counts not treated with any drugs should run for purposes of comparison. Furthermore, assays described by, e.g., Hill et al., *Brain Res.* 603:222-233 (1993).

Using these assay, one of ordinary skill in the art can readily prepare a large number of ADNF polypeptides in accordance with the teachings of the present invention and, in turn, screen them using the foregoing assay to find ADNF polypeptides, in addition to those set forth herein, which possess the neuroprotective/neurotrophic activity of the intact ADNF growth factor. For instance, using ADNF III-8 (i.e., Asn-Ala-Pro-Val-Ser-Ile-Pro-Gln; SEQ ID NO:2) as a starting point, one can systematically add, for example, Gly-, Gly-Gly-, Leu-Gly-Gly- to the N-terminus of ADNF III-8 and, in turn, screen each of these ADNF III polypeptides in the foregoing assay to determine whether they possess neuroprotective/neurotrophic activity. In doing so, it will be found that additional amino acids can be added to both the N-terminus and the C-terminus of the newly discovered active core site, i.e., Asn-Ala-Pro-Val-Ser-Ile-Pro-Gln (SEQ ID NO:2), without loss of biological activity as evidenced by the fact that the intact ADNF III growth factor exhibits extraordinary biological activity. It will be readily apparent to those of skill in the art that this discussion also applies to ADNF I polypeptides.

III. Pharmaceutical Compositions

In another aspect, the present invention provides pharmaceutical compositions comprising at least one of the previously described ADNF polypeptides comprising at least one D-amino acid within the active core site in an amount sufficient to exhibit neuroprotective/neurotrophic activity, and a pharmaceutically acceptable diluent, carrier or excipient. The pharmaceutical compositions comprising one of the previously described ADNF polypeptides are particularly useful as oral agents, as they have stability in the gastrointestinal tract and can be absorbed without change. Moreover, by using mixtures of ADNF polypeptides in L-form and in D-form for producing pharmaceutical compositions, pharmaceutical compositions possessing varying dose response properties can be obtained. These pharmaceutical compositions are useful, inter alia, in targeting different receptors that may have different affinities for ADNF polypeptides, or to provide custom tailored drug treatment regime for individuals affected by, e.g., neurodegenerative disorders.

In one embodiment, the pharmaceutical composition comprises a pharmaceutically acceptable excipient and an ADNF polypeptide, wherein the ADNF polypeptide is a member selected from the group consisting of: (a) an ADNF I polypeptide comprising an active core site having the following amino acid: Ser-Ala-Leu-Leu-Arg-Ser-Ile-Pro-Ala (SEQ ID NOl1); (b) an ADNF III polypeptide comprising an active core site having the following amino acid: Asn-Ala-Pro-Val-Ser-Ile-Pro-Gln (SEQ ID NO:2); and (c) a mixture of the ADNF I polypeptide or part (a) and the ADNF III polypeptide of part (b); wherein at least one of the ADNF I polypeptide and the ADNF III polypeptide comprises an active core site comprising at least one D-amino acid, preferably at the N-terminus and/or the C-terminus of the active core site.

In another embodiment, the pharmaceutical composition comprises a pharmaceutically acceptable excipient and an ADNF I polypeptide, wherein the active core site of the ADNF I polypeptide comprises at least one D-amino acid, preferably at the N-terminus and/or the C-terminus of the active core site. The previous discussion pertaining to the location and the number of D-amino acids within the active core site of ADNF I, as well as the discussion of additional D- and/or L-amino acids added on to the active site of the ADNF I polypeptide is fully applicable, and thus, will not be repeated with respect to this particular embodiment of the invention.

In yet another embodiment, the pharmaceutical composition comprises a pharmaceutically acceptable excipient and an ADNF III polypeptide, wherein the active core site of the ADNF III polypeptide comprises at least one D-amino acid, preferably at the N-terminus and/or the C-terminus of the active core site. The previous discussion pertaining to the location and the number of D-amino acids within the active core site of ADNF III, as well as the discussion of additional D- and/or L-amino acids added on to the active site of the ADNF III polypeptide is fully applicable, and thus, will not be repeated with respect to this particular embodiment of the invention.

In yet another embodiment, the pharmaceutical composition comprises a pharmaceutically acceptable excipient and a mixture of an ADNF I polypeptide and an ADNF III polypeptide, wherein at least one of the ADNF I and the ADNF III polypeptides comprises an active core site comprising at least one D-amino acid. The previous discussion pertaining to the location and the number of D-amino acids within the active core site of ADNF I or ADNF III, as well as the discussion of additional D- and/or L-amino acids added on to the active site of the ADNF I or ADNF III polypeptide is fully applicable, and thus, will not be repeated with respect to this particular embodiment of the invention. In yet another embodiment, the pharmaceutical composition comprises an ADNF I polypeptide comprising all D-amino acids and an ADNF III polypeptide comprising all L-amino acids. In yet another embodiment, the pharmaceutical composition comprises an ADNF I polypeptide comprising all L-amino acids and an ADNF III polypeptide comprising all D-amino acids. In yet another embodiment, the pharmaceutical composition comprises an ADNF I polypeptide comprising all D-amino acids and an ADNF III polypeptide comprising all D-amino acids.

In a pharmaceutical composition, any one or more of the ADNF I polypeptide described herein can be mixed with any one or more of the ADNF III polypeptide described herein. A mixture of an ADNF I polypeptide and an ADNF III polypeptide can be a blend of two or more of these polypeptides. A mixture of an ADNF I polypeptide and an ADNF III polypeptide can also refer to one or more of ADNF I polypeptides that are coupled to one or more of ADNF III polypeptides. For example, an ADNF I polypeptide can be covalently linked to an ADNF III polypeptide. A mixture of an ADNF I polypeptide and an ADNF III polypeptide can be prepared as a single composition and can be administered to a subject. Alternatively, an ADNF I polypeptide and an ADNF III polypeptide can be prepared as separate compositions and can be administered simultaneously or sequentially to a subject. Furthermore, different proportions of an ADNF I polypeptide and an ADNF III polypeptide can be administered to a subject. For example, in a mixture the ratio of an ADNF I polypeptide and an ADNF III polypeptide can be in the range of 1:100 to 100:1, 1:10 to 10:1, or 1:1 to 2:1.

The pharmaceutical compositions of the present invention are suitable for use in a variety of drug delivery systems. Suitable formulations for use in the present invention are found in *Remington's Pharmaceutical Sciences* (17th ed. 1985)), which is incorporated herein by reference. A brief review of methods for drug delivery is described in, e.g., Langer, *Science* 249:1527-1533 (1990), which is incorporated herein by reference. In addition, the pharmaceutical compositions comprising peptides and proteins are described in, e.g., *Therapeutic Peptides and Proteins For-* mulations, Processing, and Delivery Systems, by Ajay K. Banga, Technomic Publishing Company, Inc., Lancaster, Pa. (1995).

In a preferred embodiment, the pharmaceutical composition of the present invention is formulated for oral administration. In this embodiment, it is preferred that ADNF polypeptides comprising all D-amino acids are used. A pharmaceutically acceptable nontoxic composition is formed by incorporating any of normally employed excipients, and generally 10-95% of active ingredient and more preferably at a concentration of 25%-75%. Furthermore, to improve oral absorption of ADNF polypeptides, various carrier systems, such as nanoparticles, microparticles, liposomes, phospholipids, emulsions, erythrocytes, etc. can be used. The oral agents comprising ADNF polypeptides of the invention can be in any suitable form for oral administration, such as liquid, tablets, capsules, or the like. The oral formulations can be further coated or treated to prevent or reduce dissolution in stomach. See, e.g., *Therapeutic Peptides and Proteins, Formulation, Processing, and Delivery Systems*, by A. K. Banga, Technomic Publishing Company, Inc., 1995.

Furthermore, the ADNF polypeptides comprising at least one D-amino acid within the active core sites are embodied in pharmaceutical compositions intended for parenteral, topical, oral, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that comprise a solution of a mixture of ADNF polypeptides, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For aerosol administration, ADNF polypeptides comprising at least one D-amino acid within the active core sites are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

For solid compositions, conventional nontoxic solid carriers may be used. Solid carriers include, for example, pharmaceutical grades of mannitol, lactose, starch, magnesium stearate, sodium saccharin, talcum, cellulose, glucose, sucrose, magnesium carbonate, and the like.

Small polypeptides including SALLRSIPA (SEQ ID NO:1) and NAPVSIPQ (SEQ ID NO:2) cross the blood brain barrier. For longer polypeptides that do not cross blood the brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62-64 (1981); Peterson et al., *Biochem. Pharmacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neuro.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)). In particular, cannulas can be used to administer neurotrophic factors to mammals (see, e.g., Motta & Martini, *Proc. Soc. Exp. Biol. Med.* 168:62-64 (1981) (neurotensin); Peng et al., *Brain Res.* 632:57-67 (1993) (NGF); Anderson et al., *J. Comp. Neurol.* 357:296-317 (1995) (BDNF, NGF, neurotrophin-3).

Alternatively, longer ADNF polypeptides that do not cross blood brain barrier can be coupled with a material which assists the ADNF polypeptide to cross the blood brain barrier and to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ADNF polypeptides across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the hydrophobic domain of signal peptides, was found to have similar cell membrane translocation characteristics (see, e.g., Lin et al., *J. Biol. Chem.* 270:14255-14258 (1995)).

Examples of peptide sequences which can be linked to a ADNF polypeptide of the invention, for facilitating uptake of ADNF polypeptides into cells, include, but are not limited to: an 11 amino acid peptide of the tat protein of HIV (see Schwarze et al., *Science* 285:1569-1572 (1999)); a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ADNF polypeptides.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.,* 268:3334-3341 (1993); Perelle et al., *Infect. Immun.,* 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immuno.* 63:3851-3857 (1995); Klimpel et al., *PNAS U.S.A.* 89:10277-10281 (1992); and Novak et al., *J. Biol. Chem.* 267:17186-17193 1992)).

Such subsequences can be used to translocate ADNF polypeptides across a cell membrane. ADNF polypeptides can be conveniently fused to or derivatized with such sequences. Typically, the translocation sequence is provided as part of a fusion protein. Optionally, a linker can be used to link the ADNF polypeptides and the translocation sequence. Any suitable linker can be used, e.g., a peptide linker.

The ADNF polypeptides can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., an ADNF polypeptide.

The liposome fuses with the plasma membrane, thereby releasing the ADNF polypeptides into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the lipsome ultimately becomes permeable and releases the encapsulated compound (in this case, an ADNF polypeptide) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *PNAS* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise an ADNF polypeptide and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, *Biochim. Biophys. Acta* 443:629-634 (1976); Fraley, et al., *PNAS* 76:3348-3352 (1979); Hope et al., *Biochim. Biophys. Acta* 812:55-65 (1985); Mayer et al., *Biochim. Biophys. Acta* 858:161-168 (1986); Williams et al., *PNAS* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957,773 and 4,603,044). Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.,* 265:16337-16342 (1990) and Leonetti et al., *PNAS* 87:2448-2451 (1990).

Alternatively, nucleic acids encoding ADNF can also be used to provide a therapeutic dose of ADNF polypeptides. These nucleic acids can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

In therapeutic applications, ADNF polypeptides of the invention are administered to a patient in an amount sufficient to reduce neuronal cell death associated with various disorders, to reduce oxidative stress in a patient, or to reduce a condition associated with fetal alcohol syndrome in a subject in utero. An amount adequate to accomplish this is defined as a "therapeutically effective dose." Amounts effective for this use will depend on, for example, the particular ADNF polypeptide employed, the conditions to be treated, the type of neuronal cell death or damage to be prevented, the manner of administration, the weight and general state of health of the patient, and the judgment of the prescribing physician. For example, for the prevention or reduction of neuronal cell death, an amount of ADNF polypeptides falling within the range of a 1 μg to 50 μg, preferably 1 μg to 10 μg dose given orally once a day per mouse (e.g., in the evening) would be a therapeutically effective amount. This dose is based on the average body weight of mice, and an appropriate dose for human can be extrapolated based on the average weight of human.

IV. Methods for Reducing Neuronal Cell Death

In another aspect, the present invention provides a method for reducing neuronal cell death, the method comprising contacting neuronal cells with an ADNF polypeptide in an amount sufficient to reduce neuronal cell death, wherein the ADNF polypeptide comprises at least one D-amino acid within its active core site, preferably at the N-terminus and/or the C-terminus of the active core site. In this method, the ADNF polypeptide can be an ADNF I polypeptide, an ADNF III polypeptide, or mixtures thereof.

In one embodiment, the method comprises contacting neuronal cells with an ADNF polypeptide, wherein the ADNF polypeptide is a member selected from the group consisting of: (a) an ADNF I polypeptide comprising an active core site having the following amino acid: Ser-Ala-Leu-Leu-Arg-Ser-Ile-Pro-Ala (SEQ ID NO:1); (b) an ADNF III polypeptide comprising an active core site having the following amino acid: Asn-Ala-Pro-Val-Ser-Ile-Pro-Gln (SEQ ID NO:2); and (c) a mixture of the ADNF I polypeptide or part (a) and the ADNF III polypeptide of part (b); wherein at least one of the ADNF I polypeptide and the ADNF III polypeptide comprises an active core site comprising at least one D-amino acid.

In another embodiment, the method comprises contacting neuronal cells with an ADNF I polypeptide, wherein the active core site of the ADNF I polypeptide comprises at least one D-amino acid, preferably at the N-terminus and/or the C-terminus of the active core site. The previous discussion pertaining to the location and the number of D-amino acids within the active core site of ADNF I, as well as the discussion of additional D- and/or L-amino acids added on to the active site of the ADNF I polypeptide is fully applicable, and thus, will not be repeated with respect to this particular embodiment of the invention.

In yet another embodiment, the method comprises contacting neuronal cells with an ADNF III polypeptide, wherein the active core site of the ADNF III polypeptide comprises at least one D-amino acid, preferably at the N-terminus and/or the C-terminus of the active core site. The previous discussion pertaining to the location and the number of D-amino acids within the active core site of ADNF III, as well as the discussion of additional D- and/or L-amino acids added on to the active site of the ADNF III polypeptide is fully applicable, and thus, will not be repeated with respect to this particular embodiment of the invention.

In yet another embodiment, the method comprises contacting neuronal cells with a mixture of an ADNF I polypeptide and an ADNF III polypeptide, wherein at least one of the ADNF I polypeptide and the ADNF III polypeptide comprises an active core site comprising at least one D-amino acid. The previous discussion pertaining to the location and the number of D-amino acids within the active core site of ADNF I or ADNF III, as well as the discussion of additional D- and/or L-amino acids added on to the active site of the ADNF I polypeptide or ADNF III polypeptide is fully applicable, and thus, will not be repeated with respect to this particular embodiment of the invention.

ADNF polypeptides of the present invention can be used in the treatment of neurological disorders and for the prevention of neuronal cell death. For example, ADNF polypeptides of the present invention can be used to prevent the death of neuronal cells including, but not limited to, spinal cord neurons, hippocampal neurons, cerebral cortical neurons and cholinergic neurons. More particularly, ADNF polypeptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

As such, the ANDF polypeptides of the present invention can be used to reduce gp120-induced neuronal cell death by administering an effective amount of an ADNF polypeptide of the present invention to a patient infected with the HIV virus. The ADNF polypeptides of the present invention can also be used to reduce neuronal cell death associated with excito-toxicity induced by N-methyl-D-aspartate stimulation, the method comprising contacting neuronal cells with an ADNF polypeptide of the present invention in an amount sufficient to prevent neuronal cell death. The ADNF polypeptides of the present invention can also be used to reduce cell death induced by the β-amyloid peptide in a patient afflicted or impaired with Alzheimer's disease, the method comprising administering to the patient an ADNF polypeptide of the present invention in an amount sufficient to prevent neuronal cell death. The ADNF polypeptides can also be used to alleviate learning impairment produced by cholinergic blockage in a patient afflicted or impaired with Alzheimer's disease. For example, ADNF polypeptides can be used to improve short-term and/or reference memory in Alzheimer's patients.

Similarly, it will be readily apparent to those of skill in the art that the ADNF polypeptides of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipo-fuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

Other ADNF polypeptides (including their alleles, polymorphic variants, species homologs and subsequences thereof) that reduce neuronal cell death can be screened using the various methods described in U.S. Ser. No. 60/037,404, filed Feb. 7, 1997 (published as WO 98/35042), and U.S. Ser. No. 09/187,330 filed Nov. 6, 1998, both of which are incorporated herein by reference. For example, it will be readily apparent to those skilled in the art that using the teachings set forth above with respect to the design and synthesis of ADNF polypeptides and the assays described herein, one of ordinary skill in the art can identify other biologically active ADNF polypeptides comprising at least one D-amino acid within their active core sites. For example, Brenneman et al., *nature* 335:639-642 (1988), and Dibbern et al., *J. Clin. Invest.* 99:2837-2841 (1997), incorporated herein by reference, teach assays that can be used to screen ADNF polypeptides that are capable of reducing neuronal cell death associated with envelope protein (gp120) from HIV. Also, Brenneman et al., *Dev. Brain Res.* 51:63-68 (1990), and Brenneman & Gozes, *J. Clin. Invest.* 97:2299-2307 (1996), incorporated herein by reference, teach assays that can be used to screen ADNF polypeptides which are capable of reducing neuronal cell death associated with excito-toxicity induced by stimulation by N-methyl-D-aspartate. Other assays described in, e.g., WO 98/35042 can also be used to identify other biologically active ADNF polypeptides comprising at least one D-amino acid within their active core sites.

Moreover, ADNF polypeptides that reduce neuronal cell death can be screened in vivo. For example, the ability of ADNF polypeptides that can protect against learning and memory deficiencies associated with cholinergic blockade can be tested. For example, cholinergic blockade can be obtained in rats by administration of the cholinotoxin AF64A, and ADNF polypeptides can be administered intranasally and the water maze experiments can be performed (Gozes et al., *Proc. Natl. Acad. Sci. USA* 93:427-432 (1996), the teachings of which are incorporated herein by reference). Animals treated with efficacious ADNF polypeptides would show improvement in their learning and memory capacities compared to the control.

Furthermore, the ability of ADNF polypeptides that can protect or reduce neuronal cell death associated with Alzheimer's disease can be screened in vivo. For these experiments, apolipoprotein E (ApoE)-deficient homozygous mice can be used (Plump et al., *Cell* 71:343-353 (1992); Gordon et al., *Neuroscience Letters* 199:1-4 (1995); Gozes et al., *J. Neurobiol.* 33:329-342 (1997)), the teachings of which are incorporated herein by reference.

V. Methods for Reducing Oxidative Stress

In yet another aspect, the present invention provides methods for treating oxidative stress in a patient by administering to the patient an ADNF polypeptide in an amount sufficient to prevent or reduce oxidative stress, wherein the ADNF polypeptide comprises at least one D-amino acid within its active core site, preferably at the N-terminus and/or the C-terminus of the active core site. Oxidative stress has been implicated in several neurodegenerative diseases in humans (Cassarmno & Bennett, *Brain Res. Reviews* 29:1-25 (1999)). Moreover, oxidative stress produced from alcohol administration has been associated with fetal death and abnormalities (e.g., conditions associated with fetal alcohol syndrome). See, e.g., Henderson et al., *Alcoholism: Clinical and Experimental Research* 19:714-720 (1995). In these methods, the ADNF polypeptide can be an ADNF I polypeptide, an ADNF III polypeptide, or mixtures thereof. By using the ADNF polypeptides of the present invention, oxidative stress associated with various clinical conditions can be reduced.

In one embodiment, the method comprises treating oxidative stress in a patient with an ADNF polypeptide, wherein the ADNF polypeptide is a member selected from the group consisting of: (a) an ADNF I polypeptide comprising an active core site having the following amino acid: Ser-Ala-Leu-Leu-Arg-Ser-Ile-Pro-Ala (SEQ ID NO:1); (b) an ADNF III polypeptide comprising an active core site having the following amino acid: Asn-Ala-Pro-Val-Ser-Ile-Pro-Gln (SEQ ID NO:2); and (c) a mixture of the ADNF I polypeptide or part (a) and the ADNF III polypeptide of part (b); wherein at least one of the ADNF I polypeptide and the ADNF III polypeptide comprises an active core site comprising at least one D-amino acid, preferably at the N-terminus and/or the C-terminus of the active core site.

In another embodiment, the method comprises treating oxidative stress in a patient with an ADNF I polypeptide, wherein the active core site of the ADNF I polypeptide comprises at least one D-amino acid, preferably at the N-terminus and/or the C-terminus of the active core site. The previous discussion pertaining to the location and the number of D-amino acids within the active core site of ADNF I, as well as the discussion of additional D- and/or L-amino acids added on to the active site of the ADNF I polypeptide is fully applicable, and thus, will not be repeated with respect to this particular embodiment of the invention.

In yet another embodiment, the method comprises treating oxidative stress in a patient with an ADNF III polypeptide, wherein the active core site of the ADNF III polypeptide comprises at least one D-amino acid, preferably at the N-terminus and/or the C-terminus of the active core site. The previous discussion pertaining to the location and the number of D-amino acids within the active core site of ADNF III, as well as the discussion of additional D- and/or L-amino acids added on to the active site of the ADNF III polypeptide is fully applicable, and thus, will not be repeated with respect to this particular embodiment of the invention.

In yet another embodiment, the method comprises treating oxidative stress in a patient with a mixture of an ADNF I polypeptide and an ANDF III polypeptide, wherein at least one of the ADNF I and the ADNF III polypeptide comprises an active core site comprising at least one D-amino acid. The previous discussion pertaining to the location and the number of D-amino acids within the active core site of ADNF I or ADNF III, as well as the discussion of additional D- and/or L-amino acids added on to the active site of the ADNF I or ADNF III polypeptide is fully applicable, and thus, will not be repeated with respect to this particular embodiment of the invention.

Other ADNF polypeptides (including their alleles, polymorphic variants, species homologs and subsequences thereof) that are effective in reducing oxidative stress can be screened using primary neurons. For example, cultured embryonic neurons (E18) rat hippocampal neurons can be treated with, e.g., 0.5 µM $FeSO_4$ to induce oxidative stress. The degree of oxidative stress can be quantified by cell counting and/or morphological criteria. Furthermore, apoptosis induced by oxidative stress results in nuclear condensation and DNA fragmentation. Apoptotic nucleic can be measured by counting cells in culture stained with the fluorescent DNA-binding dye, e.g., Hoescht 33342. See Glazner et al., Society for Neuroscience 27$^{th}$ Annual Meeting, Abstracts vol. 23, part 2 (1997). To screen ADNF polypeptides comprising at least one D-amino acid that can reduce oxidative stress in vitro, $FeSO_4$ treated neurons can be contacted with various ADNF polypeptides comprising D-amino acids for sufficient time (e.g., 24 hours). Cells with apoptotic nucleic can be quantified as described above. ADNF polypeptides comprising at least one D-amino acid that reduce the quantity of apoptotic nucleic compared to control (e.g., cells untreated with ADNF polypeptides) can be used to treat oxidative stress in a patient.

Other ADNF polypeptides that are effective in reducing oxidative stress can also be screened using in vivo assays. For example, ethanol consumption is known to cause oxidative stress in vivo. In the human body, ethanol is metabolized into cytotoxic acetaldehyde by alcohol dehydrogenase enzyme in the liver and acetaldehyde is oxidized to acetate by aldehyde oxidase or xanthine oxidase giving rise to free radicals or reactive oxygen species (ROS). See, e.g., Schlorff et al., Alcohol 17:95-105 (1999). Thus, ethanol consumption can be used to induce oxidative stress in in vivo animal models (e.g., rat, mouse, human, etc.). Thereafter, animals suffering from ethanol induced oxidative stress can be used as models to screen other ADNF polypeptides comprising at least one D-amino acid that can reduce the level of oxidative stress.

The level of oxidative stress of cells and tissues of in vivo animal models can be measured using a number of assays known in the art. For example, protocols described in Schlorff et al. (1999), supra, can be used to measure effects of rat ethanol ingestion on lipid peroxidation in plasma (e.g., plasma malondialdehyde) and changes in antioxidant system (e.g., superoxide dismutase, catalase, glutathione peroxidase, glutathione reductase, etc.). Effective ADNF polypeptides are those that prevent or reduce changes in lipid peroxidation in plasma or on antioxidant system in ethanol ingested animal models compared to control (e.g., animal models untreated with ADNF polypeptides). In another example, fetal death and abnormalities (e.g., conditions associated with fetal alcohol syndrome) are considered a severe form of oxidative stress produced from alcohol administration (Henderson et al., Alcoholism: Clinical and Experimental Research 19:714-720 (1995)). Therefore, a well established model (e.g., mice) for fetal alcohol syndrome can also be used to screen for other ADNF polypeptides that can reduce oxidative stress. The use of this model for fetal alcohol syndrome and methods for reducing a condition associated with fetal alcohol syndrome are described in detail below.

VI. Methods for Reducing a Condition Associated with Fetal Alcohol Syndrome

In yet another aspect, the present invention provides a method for reducing a condition associated with fetal alcohol syndrome in a subject who is exposed to alcohol in utero, the method comprising administering to the subject an ADNF polypeptide in an amount sufficient to reduce the condition associated with fetal alcohol syndrome, wherein the ADNF polypeptide comprises an active core site comprising at least one D-amino acid, preferably at the N-terminus and/or the C-terminus of the active core site. In this method, the ADNF polypeptide can be an ADNF I polypeptide, an ADNF III polypeptide, or mixtures thereof.

Treatment of a well-characterized model for FAS (e.g., C57B1/6J mouse strain) with an ADNF polypeptide comprising at least one D-amino acid within an active core site reduces or prevents alcohol induced fetus death, body and brain weight reduction, and VIP mRNA reduction. Similarly, the human embryo, fetus, or subject can be protected from alcohol induced effects by administering an ADNF polypeptide directly to the embryo, fetus, or subject, or by administering the ADNF polypeptide indirectly to the fetus by administering it to the mother. Preferably, ADNF polypeptides are orally administered.

In one embodiment, the method comprises administering to a subject who is exposed to alcohol in utero with an ADNF polypeptide, wherein the ADNF polypeptide is a member selected from the group consisting of: (a) an ADNF I polypeptide comprising an active core site having the following amino acid: Ser-Ala-Leu-Leu-Arg-Ser-Ile-Pro-Ala (SEQ ID NO:1); (b) an ADNF III polypeptide comprising an active core site having the following amino acid: Asn-Ala-Pro-Val-Ser-Ile-Pro-Gln (SEQ ID NO:2); and (c) a mixture of the ADNF I polypeptide or part (a) and the ADNF III polypeptide of part (b); wherein at least one of the ADNF I polypeptide and the ADNF III polypeptide comprises an active core site comprising at least one D-amino acid.

In another embodiment, the method comprises administering to a subject who is exposed to alcohol in utero with an ADNF I polypeptide, wherein the active core site of the ADNF I polypeptide comprises at least one D-amino acid, preferably at the N-terminus and/or the C-terminus of the active core site. The previous discussion pertaining to the location and the number of D-amino acids within the active core site of ADNF I, as well as the discussion of additional D- and/or L-amino acids added on to the active site of the ADNF I polypeptide is fully applicable, and thus, will not be repeated with respect to this particular embodiment of the invention.

In yet another embodiment, the method comprises administering to a subject who is exposed to alcohol in utero with an ADNF III polypeptide, wherein the active core site of the ADNF III polypeptide comprises at least one D-amino acid, preferably at the N-terminus and/or the C-terminus of the active core site. The previous discussion pertaining to the location and the number of D-amino acids within the active core site of ADNF III, as well as the discussion of additional D- and/or L-amino acids added on to the active site of the ADNF III polypeptide is fully applicable, and thus, will not be repeated with respect to this particular embodiment of the invention.

In yet another embodiment, the method comprises administering to a subject who is exposed to alcohol in utero with a mixture of an ADNF I polypeptide and an ADNF III polypeptide, wherein at least one of the ADNF I and the ADNF III polypeptide comprises an active core site comprising at least one D-amino acid. The previous discussion pertaining to the location and the number of D-amino acids within the active core site of ADNF I or ADNF III, as well as the discussion of additional D- and/or L-amino acids added on to the active site of the ADNF I or the ADNF III polypeptide is fully applicable, and thus, will not be repeated with respect to this particular embodiment of the invention.

Other ADNF polypeptides (including their alleles, polymorphic variants, species homologs and subsequences thereof) comprising at least one D-amino acid within their active core sites that reduce a condition associated with fetal alcohol syndrome can be screened using a well-characterized animal model for FAS. For example, the C57B1/6J mouse strain can be used. Previous work with this strain has defined the effects of dosage and embryonic timing on maternal serum alcohol levels and embryonic effects (Webster et al., *Neurobehav. Tox.*, 2:227-34 (1980), incorporated herein by reference). Intra-peritoneal treatment allows for defined and reproducible dosages. Acute (single) dosages of alcohol can reproduce the phenotype of FAS (Webster et al., (1980), supra). Since treatment on E8 results in the highest rate of fetal anomalies and demises, and vasoactive intestinal peptide's growth regulating effects on the embryo are limited to the early post-implantation period of embryogenesis, E8 can be chosen as a test for screening neuroprotective ADNF polypeptides comprising at least one D-amino acid within their active core sites. The mice can be injected with 25% ethyl alcohol in saline (v/v) or vehicle alone at, e.g., 0.030 ml/g maternal body weight at, e.g., 9:00 a.m. on E8 (embryonic gestation day 8). Effective ADNF polypeptides can be screened by pretreating the mice 30 minutes prior to alcohol administration. In one embodiment, the dose for nasal administration for an ADNF polypeptide is about 1 µg-50 µg, preferably about 1 µg-10 µg/mouse. This dose is based on the average body weight of mice, and an appropriate dose for human can be extrapolated based on the average body weight of human.

Various parameters can be measured to determine if an ADNF polypeptide comprising at least one D-amino acid within its active core site reduces a condition associated with fetal alcohol syndrome. For example, a number of fetal demises (i.e., death) can be compared between the control (e.g., untreated with ADNF polypeptides) and a group treated with ADNF polypeptides comprising at least one D-amino acid within their active core sites. In another example, the fetal weight and fetal brain weight in the surviving E18 fetuses can be compared. In another example, the level of VIP mRNA can be compared between the control and a group treated with ADNF polypeptides comprising at least one D-amino acid within their active core sites. In another example, the degree of learning deficits can be compared between the control and a group treated with ADNF polypeptides. In another example, the glutathione level in the control and the treated group can be compared.

EXAMPLES

A. In vitro Experiments

Dissociated cerebral cortical cultures prepared as described (Brenneman & Gozes, *J. Clin. Invest.* 97:2299-2307 (1996)) were used to compare the survival-promoting actions of ADNF I and ADNF III derived peptides. Comparisons were made with the D-form of the peptide and in combination with the L-form of the peptides. The test paradigm consisted of the addition of the test peptide in cultures that were co-treated with tetrodotoxin (TTX). TTX produced an apoptotic death in these cultures and is used as a model substance to demonstrate efficacy against this "programmed cell death" and all other means that produce this type of death mechanism. The duration of the test period was 5 days, and neurons were counted and identified by characteristic morphology and by confirmation with an immunocytochemical marker for neurons: neuron specific enolase.

Figure 2A:
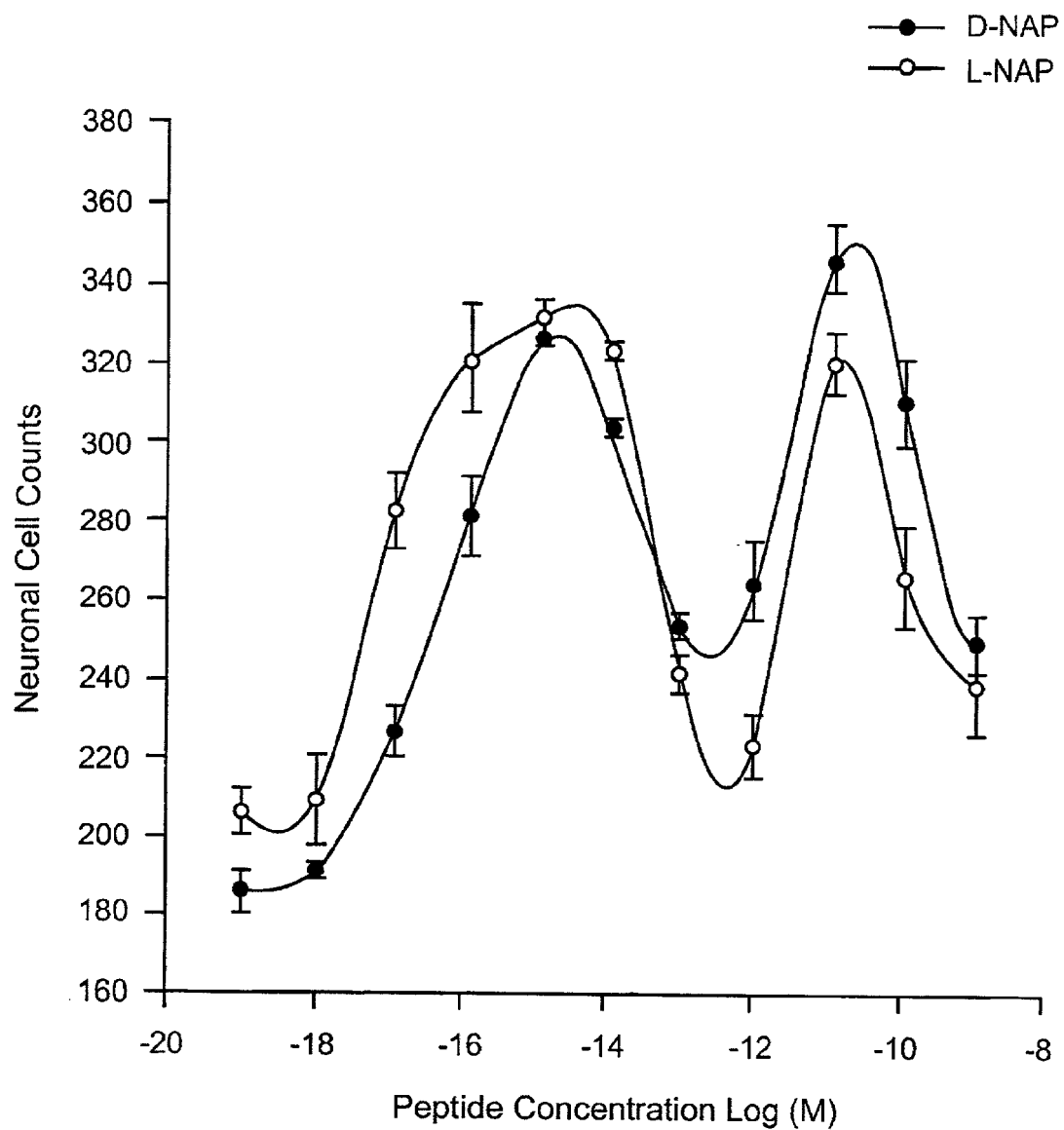
FIG. 2A compares the survival-promoting activity of D- and L-forms of NAPVSIPQ (SEQ ID NO:2) in dissociated cerebral cortical cultures treated with 1 μM tetrodotoxin. Experimental conditions were as described for FIG. 1.

As shown in FIG. 1, the D- and L-forms of SALLRSIPA (SEQ ID NO:1) (SAL) were identical in both potency and efficacy in preventing neuronal cell death associated with electrical blockade with TTX. Each point is the mean of at least three determinations, the error bars are the standard errors. Similarly, the D- and L-forms of NAPVSIPQ (SEQ ID NO:2) (NAP) were very similar, with each exhibiting a complex dose response with two apparent maxima (FIG. 2A). Unless indicated as otherwise, L-SAL and D-SAL refer to a peptide having an amino acid sequence of Ser-Ala-Leu-Leu-Arg-Ser-Ile-Pro-Ala (SEQ ID NO:1) comprising all L-amino acids or all D-amino acids, respectively. Also, L-NAP and D-NAP refer to a peptide having an amino acid sequence of Asn-Ala-Pro-Val-Ser-Ile-Pro-Gln (SEQ ID NO:2) comprising all L-amino acids or all D-amino acids, respectively.

Figure 2B:
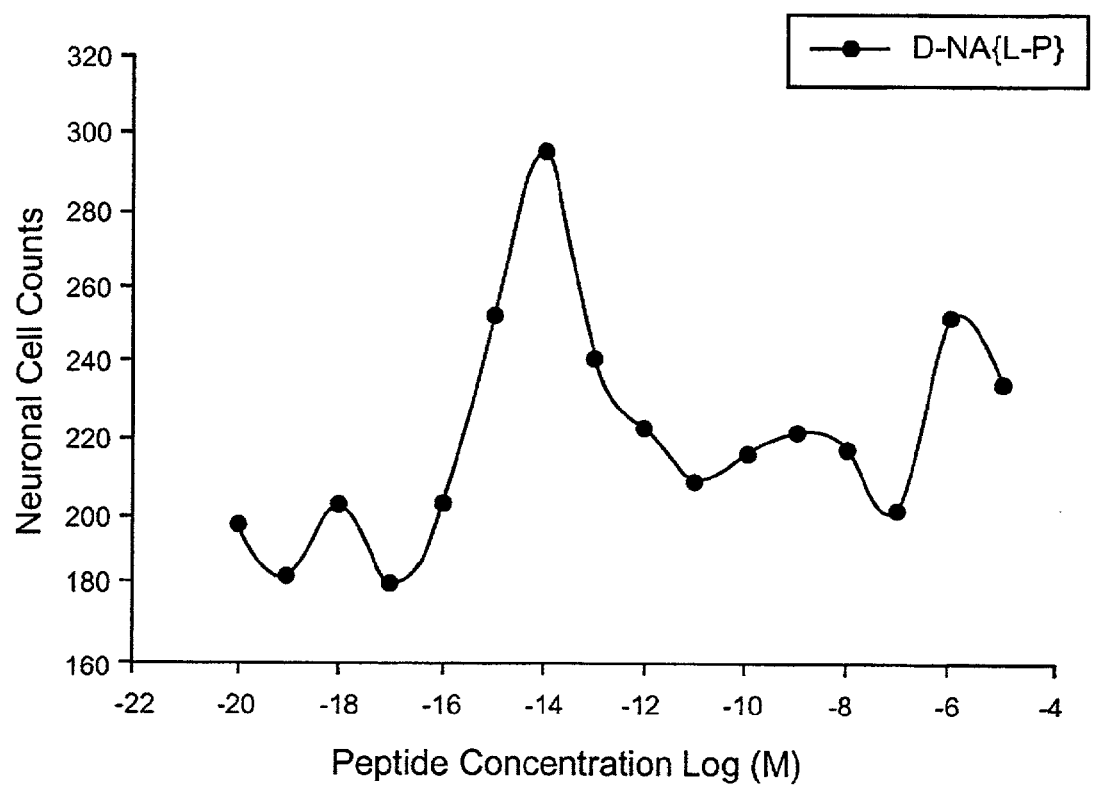
FIG. 2B illustrates the effect of a mixture of D- and L-amino acid D-NA {L-P} VSIPQ on survival promoting activity in cerebral cortical culture co-treated with tetrodotoxin for 5 days. In peptide NAPVSIPQ (SEQ ID NO:2), all of the amino acids were in the D-form, except the third proline residue was in the L-form.

In FIG. 2B, the effect of an ADNF peptide that has amino acid residues in both L-form and in D-form, namely D-NA{L-P}VSIPQ, was tested. In this ADNF peptide, all of the amino acids of NAPVSIPQ (SEQ ID NO:2) were in the D-form, except the third proline residue was in the L-form. Cerebral cortical cultures were treated with 1 µM TTX for 5 days, which is a model of apoptotic death that is relevant to neurodegenerative disease. Cultures treated with the toxin were given various concentrations of D-NA{L-P}VSIPQ. As all L- and all D-amino acid NAPVSIPQ (SEQ ID NO:2), this mixed D/L peptide D-NA{L-P}VSIPQ retained survival-promoting activity and was effective in cell culture in preventing neuronal cell death in the TTX model.

Figure 3A:
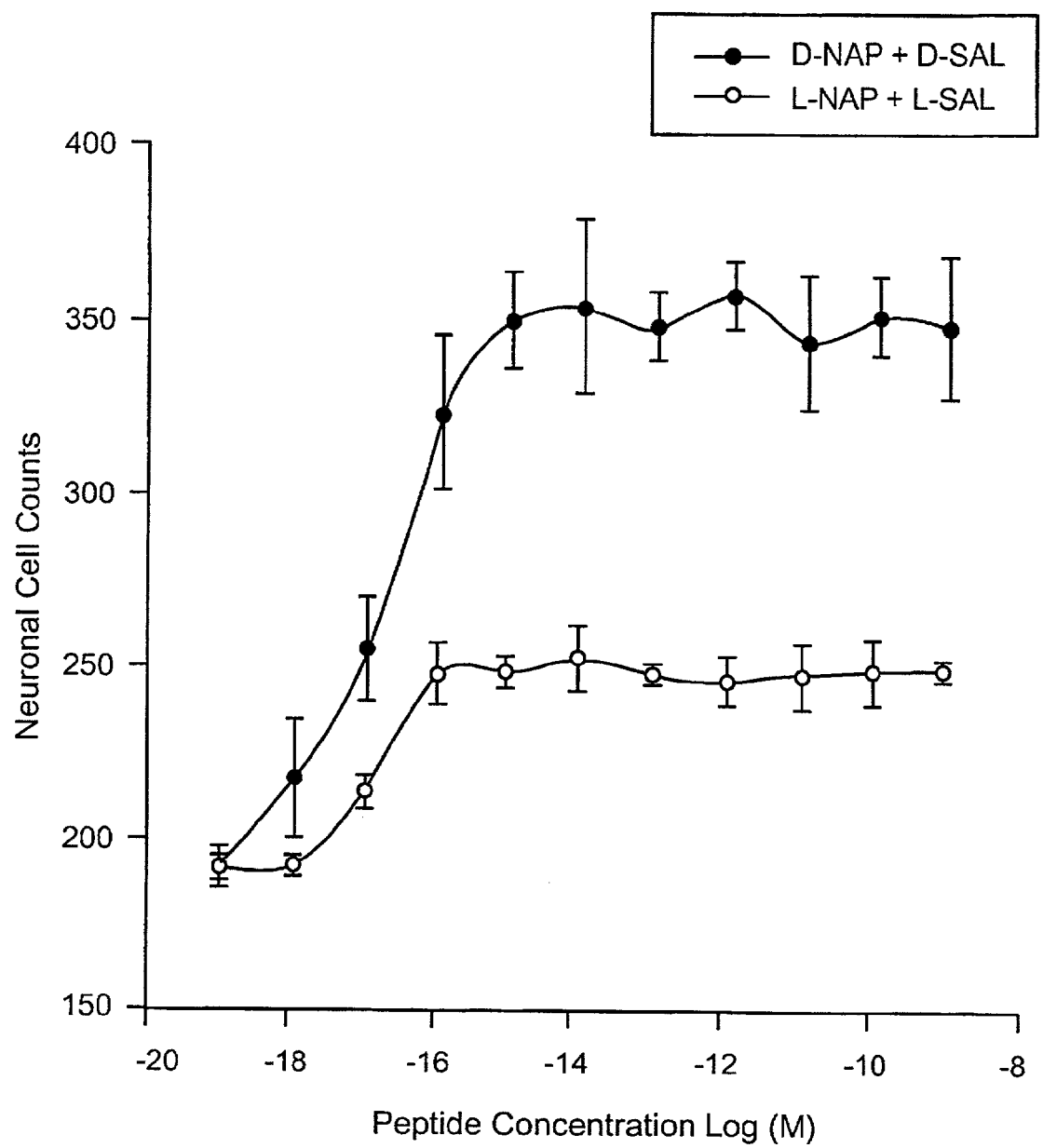
FIG. 3A compares the survival-promoting activity of combinations of NAPVSIPQ (SEQ ID NO:2) and SALLRSIPA (SEQ ID NO:1) in D- and L-forms. Experimental conditions were as described for FIG. 1.
Figure 3B:
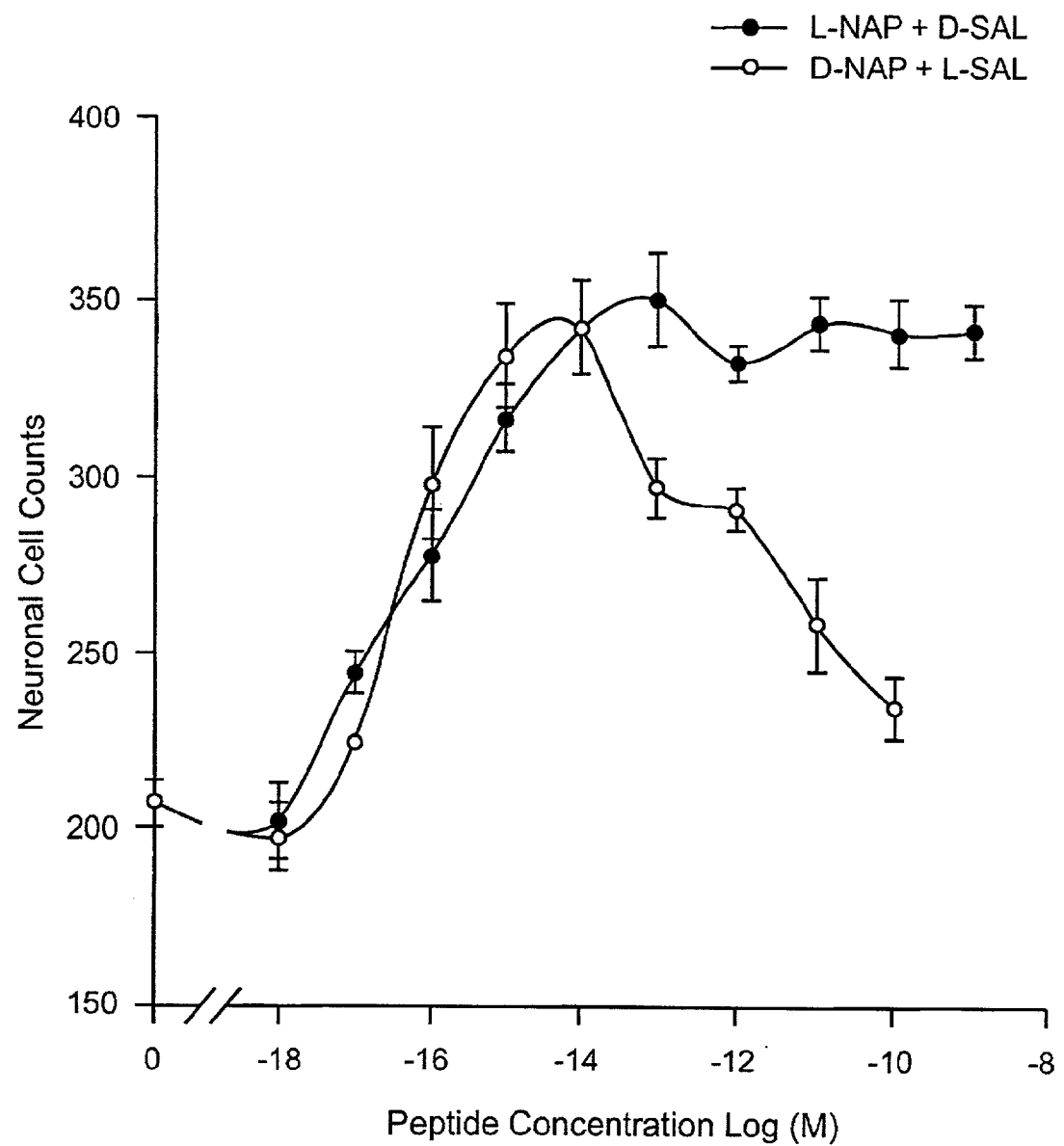
FIG. 3B compares the survival-promoting activity of combinations of L-NAPVSIPQ (SEQ ID NO:2)+D-SALLRSIPA with D-NAPVSIPQ and L-SALLRSIPA (SEQ ID NO:1). Experimental conditions were as described for FIG. 1.

As illustrates in FIGS. 3A and 3B, combinations of peptides were also tested. For all combinatorial experiments, the two peptides are given in equimolar amounts. In FIG. 3A, the effect of D-NAP and D-SAL was shown to produce a different dose response from that observed with either agent alone. Importantly, there was no apparent attenuation of the survival-promoting activity at higher concentration of peptide. This apparent synergy between the peptides is significant because it indicates that there may be a broader therapeutic range of effective concentrations if both D-peptides are used combinatorially. Similar experiments conducted with both L-SAL and L-NAP resulted in significant loss of efficacy, although synergy was still evident (FIG. 3A).

Another series of experiments were conducted to show the effect of combining L- and D-forms of NAP and SAL. As shown in FIG. 3B, the use of L-NAP and D-SAL showed full efficacy and high potency in preventing apoptotic death of neurons treated with TTX. There was no apparent attenuation of the protective activity at high concentrations (>1 pM) of peptide; i.e., synergy was again evident. In contrast, treatment with D-NAP and L-SAL resulted in full efficacy but attenuation of the survival-promoting activity at concentration >0.1 pM. These data indicate specificity for combinations of D and L-peptides.

Figure 4:
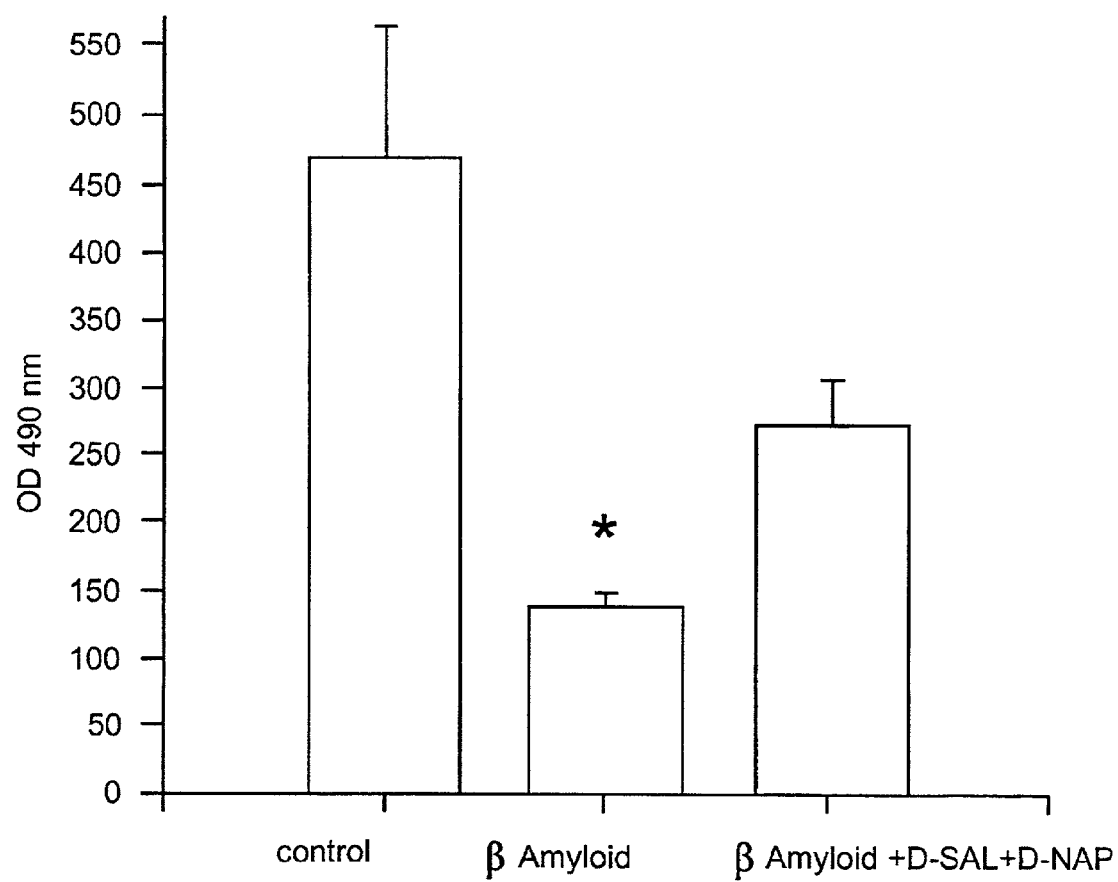
FIG. 4 illustrates that combinations of D-SALLRSIPA+D-NAPVSIPQ can protect against beta amyloid toxicity in PC12 cells.

FIG. 4 illustrates that ADNF polypeptides can protect against beta amyloid toxicity in vitro. PC12 cells (Solomon et al., *Proc. Natl. Acad. Sci. USA* 94:4109-4112 (1997)) were maintained in DMEM (Dulbecco's modified Eagles medium) supplemented with 8% horse serum, 8% heat-inactivated fetal calf serum, 2 mM L-Glutamine, (all purchased from Sigma, Rehovot, Israel), 100 mgr/ml streptomycin and 100 U/l penicillin (Biological Industries, Beit Haemek, Israel). Cultures were maintained at 37° C./5% $CO_2$ as monolayers in 75 cm² flasks and were split at a 1:12 ratio twice a week. For the beta amyloid (amino acids 25-35) treatment, seeding was at $1.5 \times 10^5$ cells/ml on 96-well plates (100 ml/well) in a medium containing: DMEM supplemented with 1% Penicillin/Streptomycin, 0.5M insulin (Sigma, Rehovot, Israel). Twenty-four hours after the addition of peptides 10-9 M (D-SAL and D-NAP in a 1:1 mixture diluted to final concentration of 1 nM), beta amyloid was added at 2.5 mM and cell viability (metabolic activity) was measured 48 hours later. Metabolic activity was measured by a colorimetric method using a tetrazolium compound (3-(4,5-dimethylthiazol-2-yl-5-(3-carboxymethoxyphenyl)-2-(4-sulfophenyl)-2H tetrazlium (MTS) and an electron coupling reagent phenazine methasulfate. MTS is bioreduced by the living cells to the Formazan form, that is detected at 490 nm (Promega, Medison Wis., USA). Results showed significant activity loss in the presence of the toxin and protection by the peptides D-SAL+D-NAP.

B. In vivo Experiments

A variety of experimental models were utilized to demonstrate the efficacy of D-NAP and D-SAL in animals. Various routes of administration were employed in both rats and mice.

1. Fetal Alcohol Syndrome (FAS) in Mice

A well established model for FAS was used to test the efficacy of ADNF I and ADNF III peptides in mice (Webster et al., *Neurobehav. Tox.* 2:227-234 (1980), incorporated herein by reference). This test is designed to test for efficacy against severe oxidative stress produced from alcohol administration (Amini et al., *Free Radical Biology and Medicine* 21:357-365 (1996); Schlorff et al., *Alcohol* 17:97-105 (1999)). Fetal death and abnormalities are associated with the generation of free radicals and oxidative damage (Henderson et al., *Alcoholism: Clinical and Experimental Research* 19:714-720 (1995)). The model was chosen in that it allowed for a rapid and relevant evaluation of agents efficacious against severe oxidative stress. Since oxidative stress has been implicated in several neurodegenerative diseases in humans (Cassarmno & Bennett, *Brain Res. Reviews* 29:1-25 (1999)), efficacy in FAS can be of predictive value in the treatment of human disease.

A single injection of 25% ethyl alcohol in saline was given intraperitoneally at 0.030 ml/g body weight to pregnant mice at embryonic day 8. In the first series of experiments, peptides were given 30 minutes prior to the administration of alcohol. Dosages of 2 µg or 20 µg were given. D-NAP or L-NAP (0.5 mg) was dissolved in 50 µl of dimethyl sulfoxide and diluted with filtered (0.22µ) Dulbecco's phosphate buffered saline (DPBS) to a final volume of 5 ml. The injection volume was 200 µl. D-SAL or L-SAL was dissolved in DPBS before administration. The litter mean was used as a single measurement for statistical analysis. The average litter size was 8 and it did not differ among treatment groups.

Figure 5:
FIG. 5 illustrates that pretreatment with D-NAP, D-SAL, or L-NAP+D-SAL prevents fetal demises. At E18, the number of living and demised embryos was counted and the percentage of demises was calculated. Treatment with alcohol was given on E8, pretreatment with peptides given 30 minutes prior. Comparisons are made to the alcohol group, overall ANOVA p<0.001. Post hoc Fishers tests were performed, with the *groups significantly different than alcohol (all post-hoc p≦0.03). The sample sizes were control (36), alcohol (41), D-NAP (20 μg)+alcohol (14), D-SAL (20 μg)+alcohol (19), D-SAL (2 μg)+alcohol (8), L-NAP (20 μg)+D-SAL (20 μg)+alcohol (23).
Figure 6A:
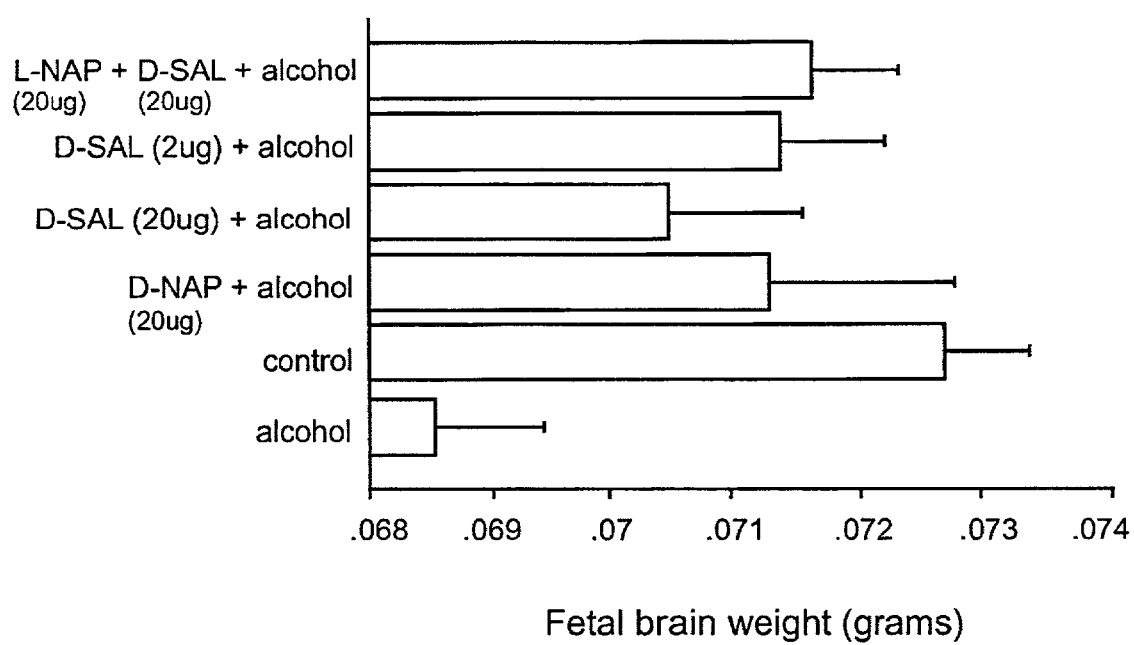
FIG. 6A illustrates that pretreatment with L-NAP+D-SAL prevented fetal microcephaly. Fetal brain weights for each pregnant female was obtained at E18. Comparisons are made to the alcohol group, overall ANOVA P value p=0.01. Sample size was the number of litters. The mean from each litter was used for statistical analysis and represents on average 8-10 fetuses. The sample sizes were control (34), alcohol (32), D-NAP (20 μg)+alcohol (13), D-SAL (20 μg)+alcohol (19), D-SAL (2 μg)+alcohol (8), L-NAP (20 μg)+D-SAL (20 μg)+alcohol (23).
Figure 6B:
FIG. 6B illustrates that pretreatment with L-NAP+D-SAL prevented or reduced fetal growth restriction. Fetal weights for each pregnant female were obtained at E18. Comparisons are made to the alcohol group, overall ANOVA P value p=0.04. Sample size was the number of litters. The mean from each litter was used for statistical analysis and represents on average 8-10 fetuses. The sample sizes were control (34), alcohol (32), D-NAP (20 µg)+alcohol (13), D-SAL (20 µg)+alcohol (19), D-SAL (2 µg)+alcohol (8), L-NAP (20 µg)+D-SAL (20 µg)+alcohol (23).

Evaluation of the surviving fetuses was done on embryonic day 18. Evaluation of efficacy was by the number of surviving fetuses (FIG. 50, brain weight (FIG. 6A) and total fetal body weight (FIG. 6B). As shown in FIG. 5, treatment with alcohol resulted in 37% fetal demise in comparison to 6% in controls. pretreatment with 20 µg D-NAP, D-SAL or L-NAP+D-SAL (20 µg each) significantly reduced the fetal demise rate in comparison to those in the alcohol group (P<0.03). As shown in FIG. 6A, of the surviving fetuses whose mother had been treated with alcohol, only those co-treated with L-NAP and D-SAL had significantly greater brain weights in comparison to those in the alcohol group. Similar protective effects of L-NAP and D-SAL were evident as assessed by total fetal weights (FIG. 6B).

Figure 7:
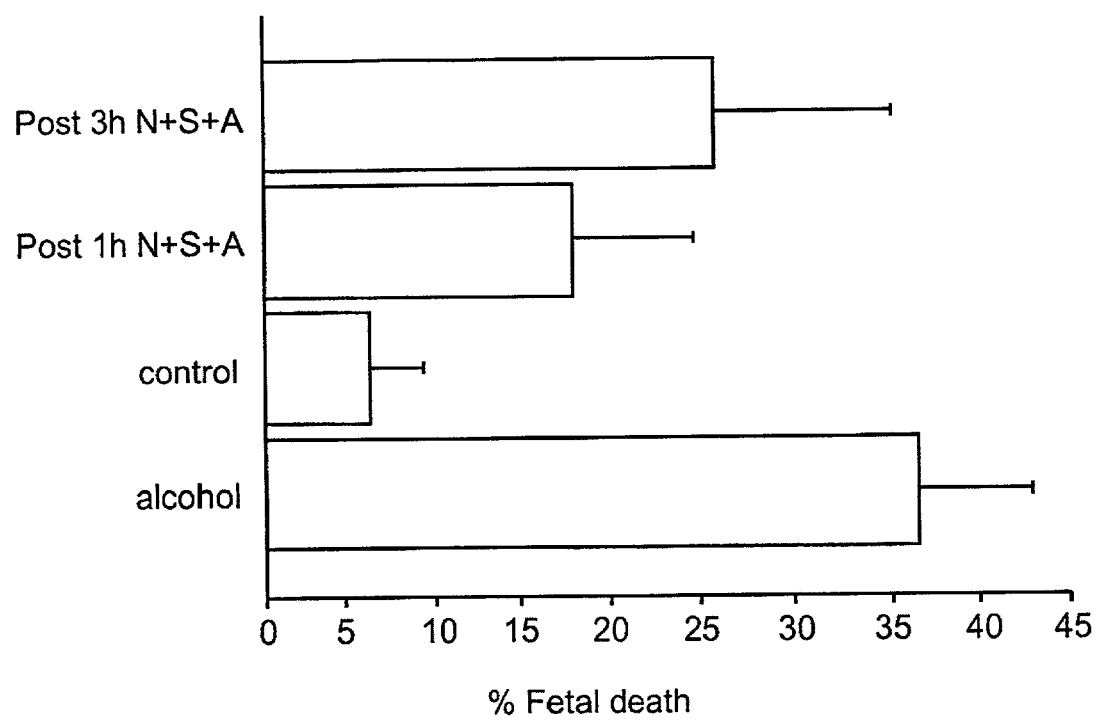
FIG. 7 illustrates that one hour post-treatment with L-NAP and L-SAL prevented fetal death. L-NAP (20 µg) and L-SAL (20 µg) were given at one and three hours after alcohol administration on E8. Comparisons are made to the alcohol group, overall ANOVA p=0.001. Post hoc Fishers tests were performed, with the one-hour and control groups significantly different than alcohol (p<0.001 and p=0.04, respectively). The sample sizes were control (36), alcohol (41), post one hour treatment (18) and post three hour treatment (14).
Figure 8:
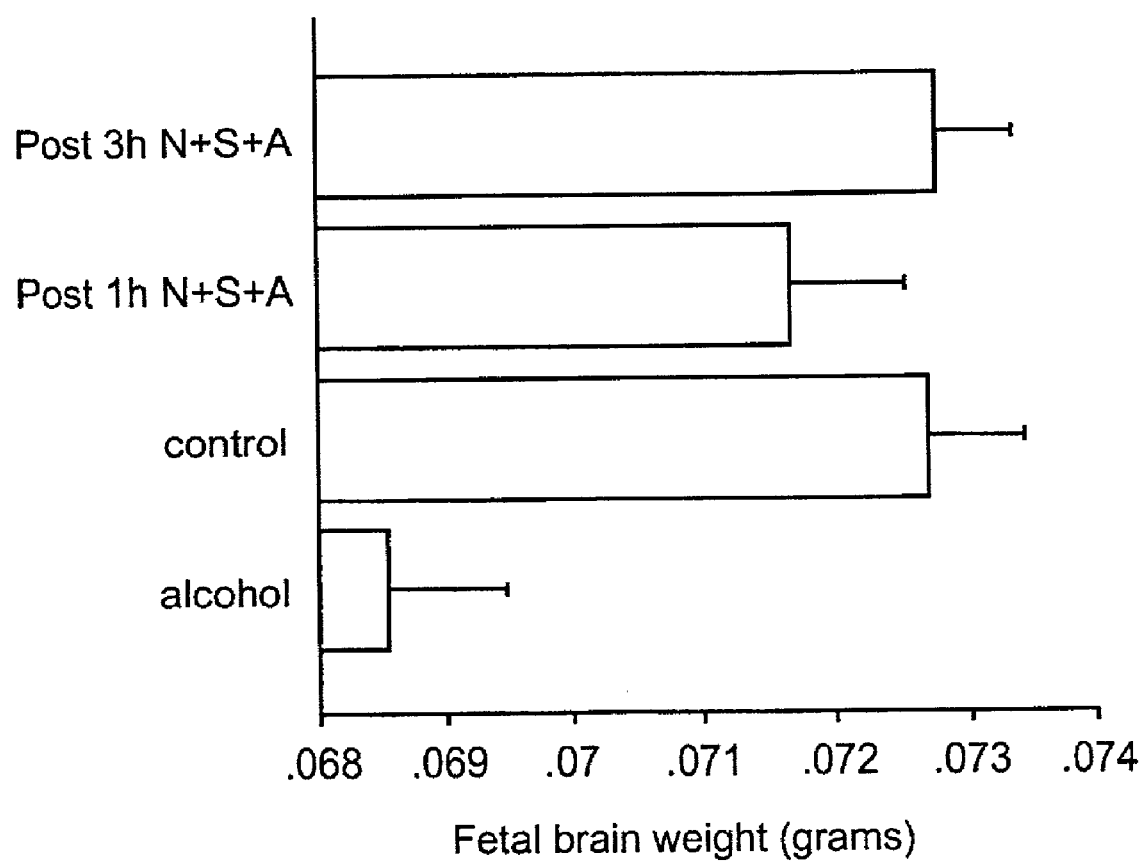
FIG. 8 illustrates that one and three hour post-treatments with L-NAP and L-SAL prevented fetal microcephaly. L-NAP and L-SAL were given at one and three hours after alcohol administration on E8 (N+S+A). Comparisons are made to the alcohol group, overall ANOVA P=0.001. Post hoc Fishers tests were performed, with the one-hour, three hour, and control groups significantly different than alcohol (p<0.001, <0.03 and P<0.008 respectively). The sample sizes were control (34), alcohol (32), post one hour treatment (17) and post three hour treatment (11).

To test for a critical period of peptide administration that could still produce an effective intervention, L-NAP (20 µg)+L-SAL (20 µg) were administered one hour or three hours after alcohol treatment of pregnant mice at gestational day E8. As shown in FIG. 7, post-treatment at 1 hour with NAP+SAL prevented the demises observed with alcohol treatment; however, post-treatment at 3 hours did not result in significant prevention of fetal demise to control levels. In addition, post-treatment with NAP+SAL (1 hour and 3 hours) prevented the microcephaly (FIG. 8), but not the growth restriction associated with FAS.

Figure 9:
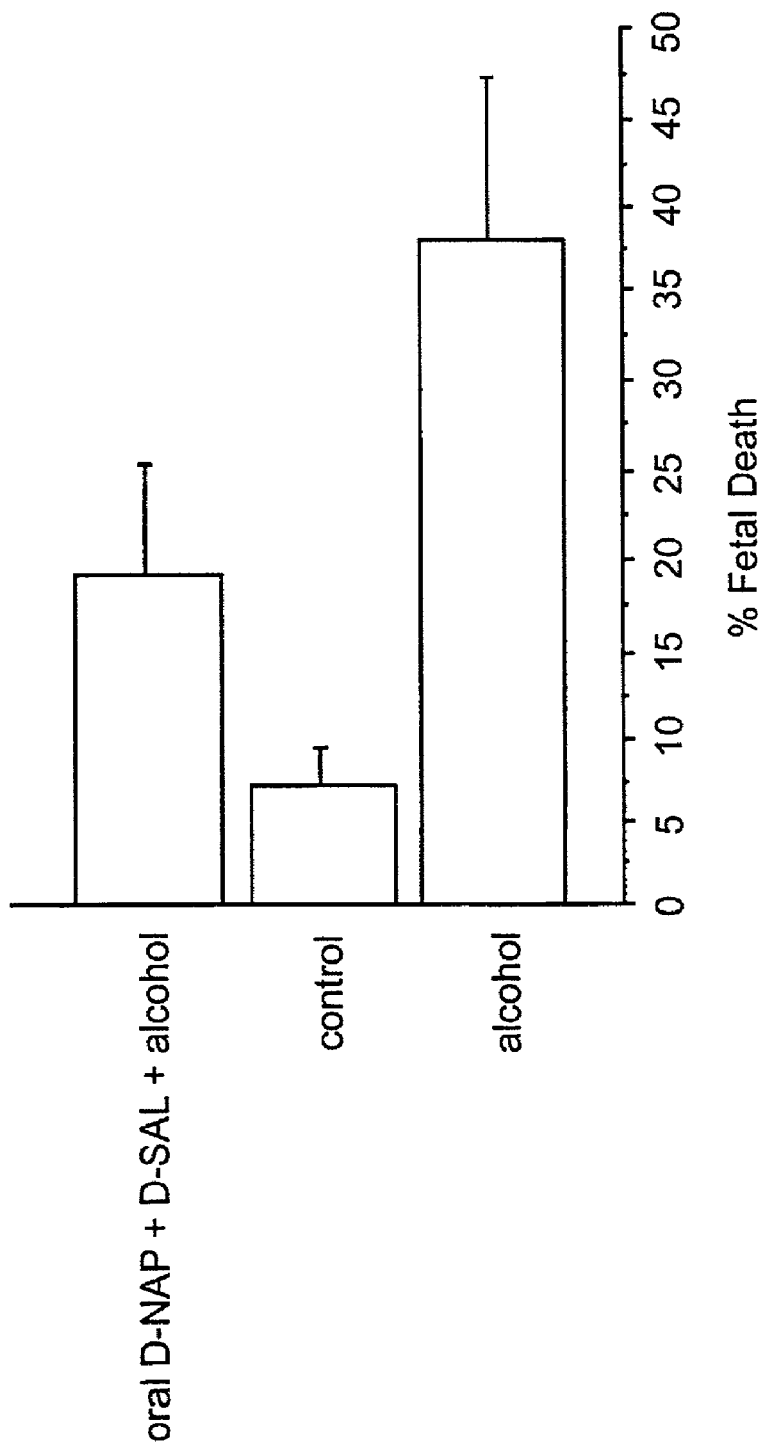
FIG. 9 illustrates that oral treatment with D-NAP and D-SAL prevented fetal death associated with fetal alcohol syndrome. D-NAP and D-SAL were given by gavage immediately after alcohol treatment on E8. Comparisons are made to the alcohol group, overall ANOVA p=0.004. Post hoc Fishers tests were performed, with the oral treatment and control groups significantly different than alcohol (p<0.001 and ≦0.04 respectively). The sample sizes were control (21), alcohol (18), oral D-NAP+D-SAL and alcohol (18).

To demonstrate that D-NAP and D-SAL were effective through oral administration, the peptides were given by gavage (i.e., introducing peptides into the stomach by a tube) to pregnant mice at gestational age day 8. As shown in FIG. 9, a significant increase in fetal survival was observed after oral treatment with 40 µg each of D-NAP and D-SAL. This is the first demonstration of an orally active embryo-protecting action of a peptide.

Figure 10A:
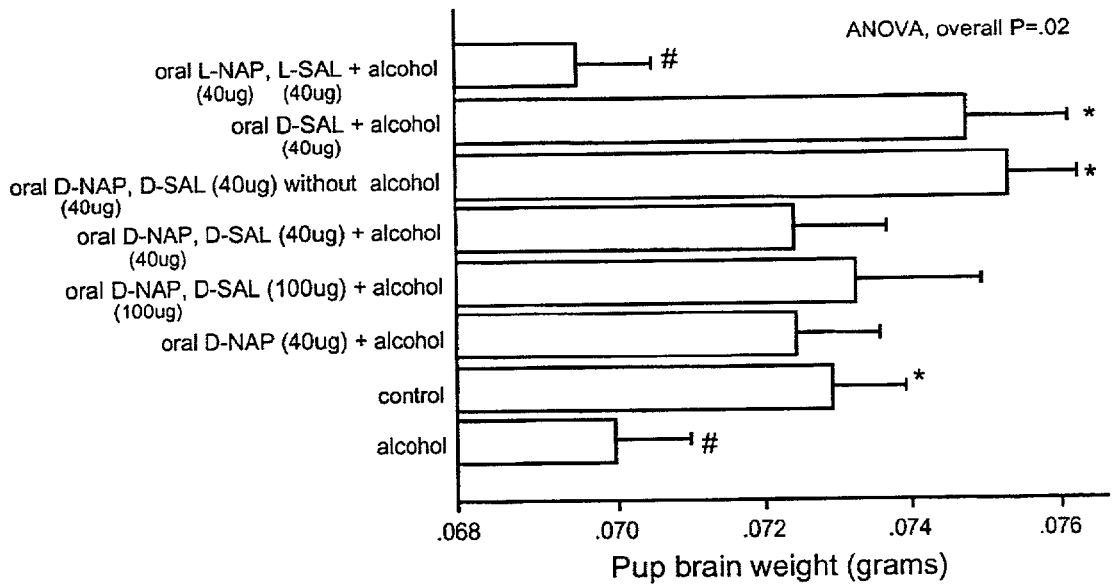
FIG. 10A illustrates the effects of oral administration of ADNF polypeptides on pup brain weight. Pregnant mice were injected with alcohol as a model for fetal alcohol syndrome according to methods of Webster et al., *Neurobehav. Tox.* 2:227-34 (1980). The pregnant mice were injected 25% alcohol at 0.030 ml/g body weight. Peptide was dissolved in phosphate-buffered saline and administered orally by gavage 30 minutes prior to alcohol treatment. The dosage of peptides NAP and SAL administered to each mouse is shown in the figure. Error bars are ±1 standard errors: * notes significant versus alcohol; and # notes significant versus control.
Figure 10B:
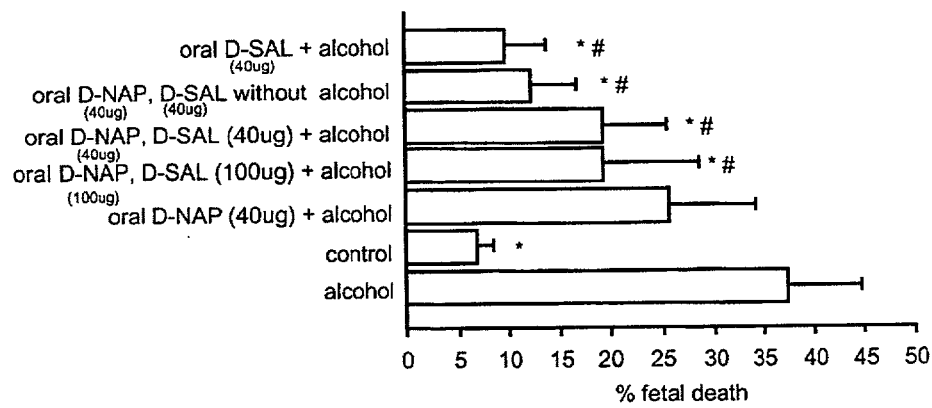
FIG. 10B illustrates the effects of oral administration of ADNF polypeptides on fetal death. Pregnant mice were treated as described above in the description for FIG. 10A. The dosage of peptides NAP and SAL administered to each mouse is shown in the figure. Error bars are ±1 standard errors; * notes significant difference versus alcohol; and # notes significant difference versus control.

FIGS. 10A and 10B illustrates effects of oral administration of ADNF polypeptides on pup brain weight and fetal death. Pregnant mice were injected with alcohol as a model for fetal alcohol syndrome according to methods of Webster et al. (1980), supra. The pregnant mice were injected 25% alcohol at 0.030 ml/g body weight. peptide was dissolved in phosphate-buffered saline and administered orally by gavage 30 minutes prior to alcohol treatment. D-SAL (all D-amino acids of SALLRSIPA (SEQ ID NO:1) at 40 µg was found to prevent fetal death as assessed on E18.

2. Apo E Knockout Mice: Developmental Behavior Assays

Recent studies have demonstrated that the inheritance of the lipid carrier apolipoprotein E4 (ApoE4) is a major risk factor in Alzheimer's disease (Strittmatter & Roses, *Proc. Natl. Acad Sci. USA* 92:4725-4727 (1995)). These studies, along with the investigations of ApoE-deficient animals indicated that an apolipoprotein E functioning system is required for normal neurodevelopment and function (Masliah et al., *J. Exp. Neurol.* 136:107-122 (1995)). The acquisition of developmental milestones of behavior requires appropriate synapse formation and proper brain conductivity (Altman et al., *Anim. Behav.* 23:896-920 (1975)). ApoE-deficient animals have been shown to be developmentally retarded (Gozes et al., *J. Neurobiol.* 33:329-342 (1997), incorporated herein by reference) offer a test system for the in vivo effects of putative neurotrophic substances, such as S-SAL and D-NAP.

Figure 11:
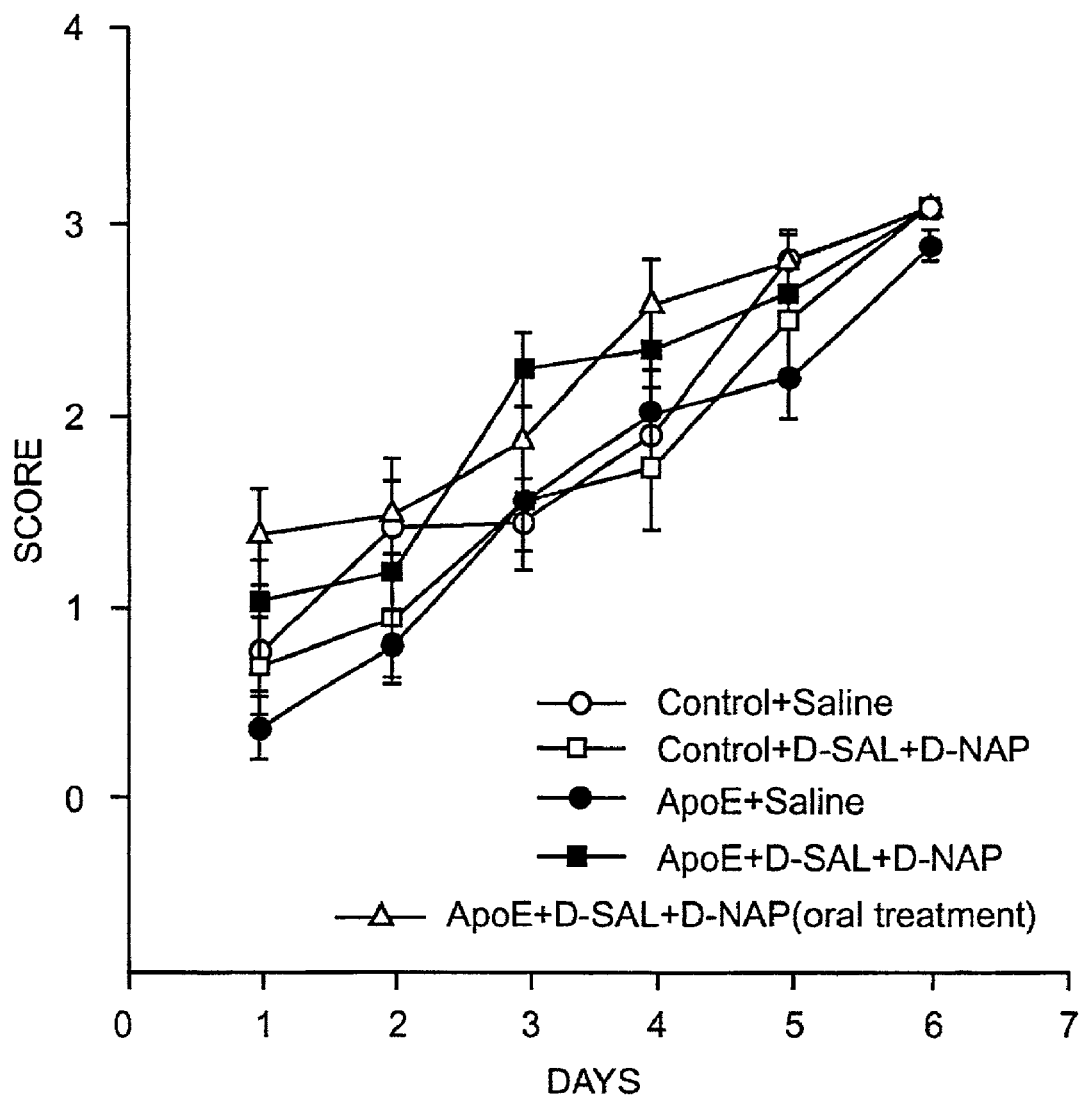
FIG. 11 illustrates development of cliff avoidance behavior in newborn mice: comparison of peptide drug response in control vs. Apo-E knock-out mice. Animals were treated either by oral application, or subcutaneous injection of D-SAL+D-NAP. Peptides (0.5 mg each) were dissolved in 0.01M acetic acid (30 µl) and 470 µl saline. Further dilutions were performed in saline. For both applications, 0.5 µg of each of the test drugs were delivered; for the oral application (sublingual), in 10 µl saline and for the injection in 20 µl. This protocol was used for the first 4 days of life. From day 5-10, the amount of the peptides and the solution volume was doubled. From day 11-14, the amount of peptide was 2 µg each in 40 µl (oral) and 80 µl (injection). Tests performed daily included cliff avoidance, negative geotaxis, placing and righting behaviors. Both subcutaneous and oral administration of D-NAP and D-SAL were compared.
Figure 12:
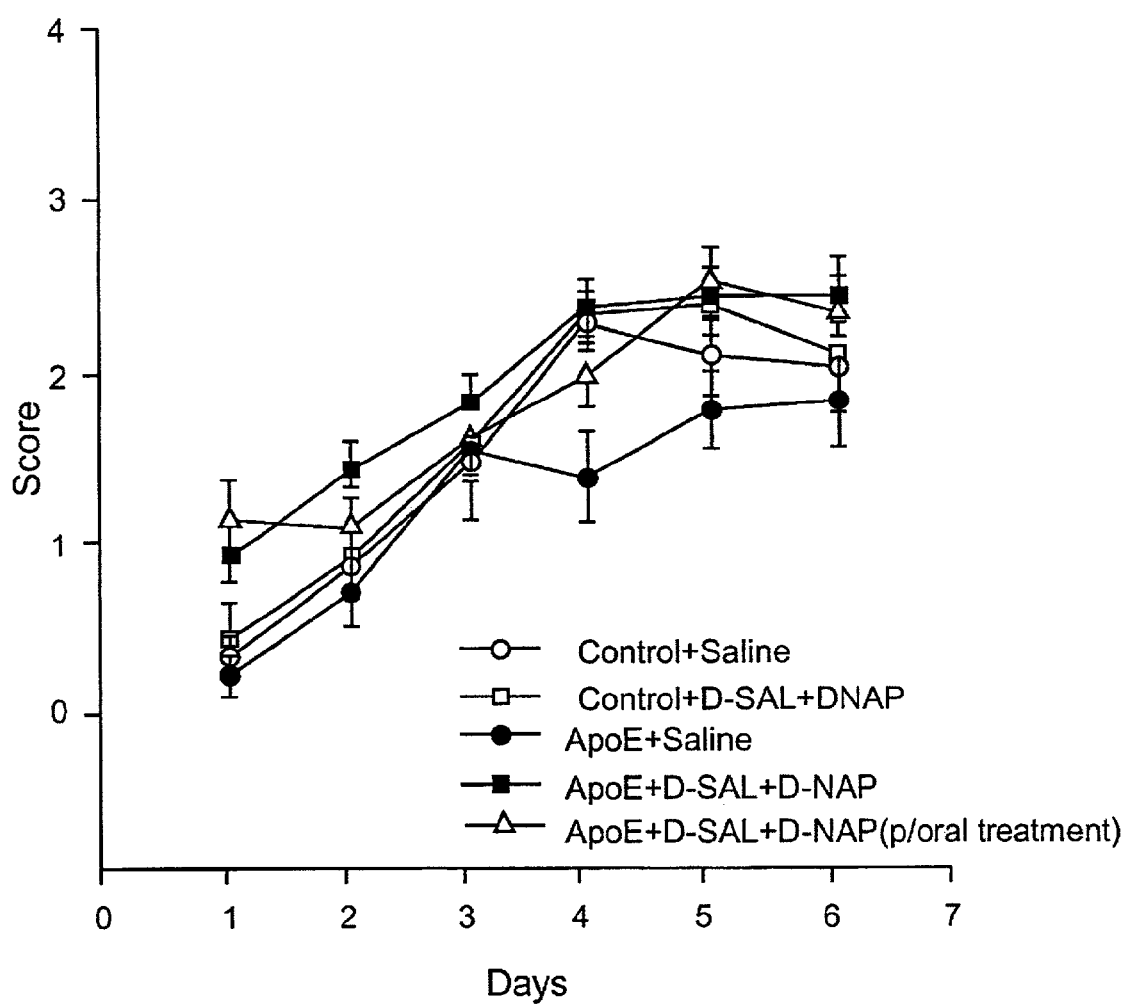
FIG. 12 illustrates development of negative geotaxis behavior in newborn mice: comparison of peptide drug responses in control vs. Apo-E knock-out mice. Treatment paradigm was as described in FIG. 11.
Figure 13:
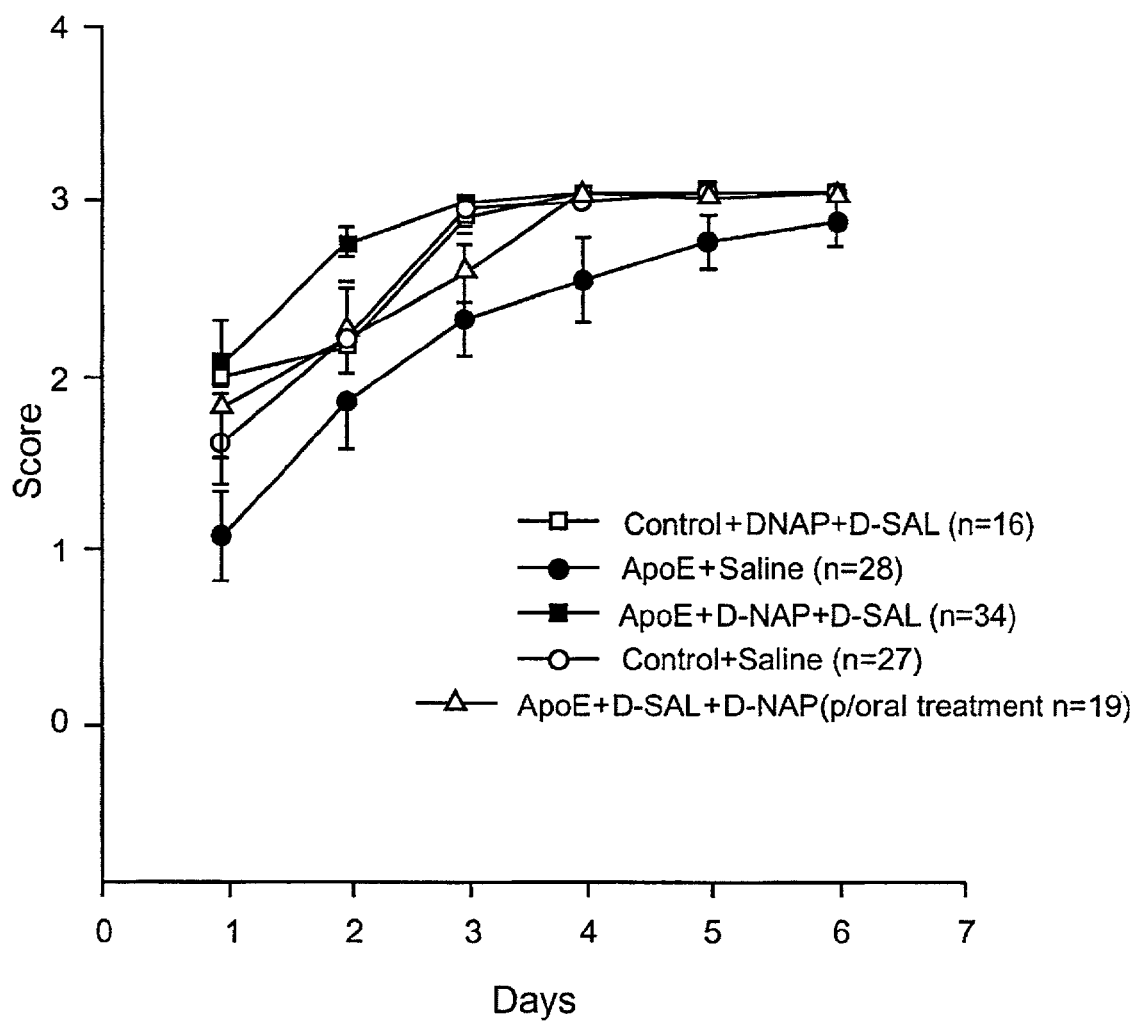
FIG. 13 illustrates development of placing behavior in newborn mice: comparison of peptide drug responses in control vs. Apo-E knock-out mice. Treatment paradigm was as described in FIG. 11.

Newborn animals were tested for the onset neurobehavioral developmental milestones as previously described (Gozes et al., *J. Neurobiol.* 33:329-342 (1997); Bassan et al., *J. Neurochem.* 72:1283-1293 (1999)). For these experiments, animals were treated either by oral application, or subcutaneous injection of D-SAL+D-NAP. Peptides (0.5 mg each) were dissolved in 0.01M acetic acid (30 microliters). For both applications, 0.5 microgram of each of the test drugs were delivered; for the oral application (sublingual), in 10 microliter saline and for the injection in 20 microliters. This protocol was used for the first 4 days of life. From day 5-10, the amount of the peptides and the solution volume was doubled. From day 11-14, the amount of peptide was 2 microgram each in 40 microliter (oral) and 80 microliter (injection). Tests performed daily included cliff avoidance, negative geotaxis, placing and righting behaviors. Both subcutaneous and oral administration of D-NAP and D-SAL were compared. As shown in FIG. 11, the slowest responders for cliff avoidance were the apoE knockout animals. This confirms previous studies which show that the behavioral developmental and learning is delayed in these animals in comparison to control animals (Gozes et al., *J. Neurobiol.* 33:329-342 (1997); Bassan et al., *J. Neurochem.* 72:1283-1293 (1999)). Administration of D-NAP+D-SAL by either subcutaneous injection or oral administration resulted in significant increases in the behavioral score, indicative of a more rapid acquisition of this developmental milestone. Similar effects were observed for negative geotaxis (FIG. 12) and placing behavior (FIG. 13).

More detailed evaluation of the results is as follows. In the following, one way analysis of variance with multiple comparison of the means (Student-Newman-Keuls method) were used for statistical comparisons.

1. FIG. 11 (cliff avoidance): the difference between apoE-deficient mice and control animals was apparent only on the fifth day of life ($P<0.001$). Injection of D-peptides to control, resulted in no effect, while injection to the deficient mice resulted in an effect only on the third day. Oral application resulted in a significant improvements only on the first day, in the deficient mice.

2. FIG. 12 (negative geotaxis): While there was no difference on the first day between control and apoE-deficient (with perhaps a difference on day three, $p<0.006$), treatment of the latter (injection or oral) resulted in significant improvements with injection on days 1, 2, 4 and 5, and with oral treatment on days 1 and 5. ($P<0.001$).

3. FIG. 13 (placing): The difference between apoE-deficient mice and control animals was apparent only on the first day of life ($P<0.001$). Similarly, oral application of the peptide mixture was efficient in enhancing the response only on the first day of life.

3. AF64A Cholinotoxicity in Adult Rats

Another focus of the present invention are the neuroprotective properties of the D-SAL and D-NAP in animals exposed to the cholinotoxin, ethylcholine aziridium (AF64A), a blocker of choline uptake (Fisher et al., *Neurosci. Lett.* 102:325-331 (1989)). An intact cholinergic system is required for normal brain function, whereas Alzheimer's disease is associated with the death of cholinergic cells (Brumback & Leech, *J. Okla. State Med. Assoc.* 87:103-111 (1994)). Rats treated with AF64A provide an accepted model for testing in vivo efficacy of cholinergic-enhancing drugs.

Although the identity of the ADNF-dependent neurons has not been fully characterized, previous studies indicated that some cholinergic neurons are among those affected (Gozes et al., *Brain Res. Dev.* 99:167-175 (1997)). In this context, ApoE-deficient mice (described above) exhibited reduced choline acetyl transferase activity (Gordon et al., *Neurosci. Lett.* 199:1-4 (1995); Gozes et al., *J. Neurobiol.* 33:329-342 (1997)) and treatment with L-NAP significantly increased cholinergic function to control levels (Bassan et al., *J. Neurochem.* 72:1283-1293 (1999)) while L-SAL treatment was less effective.

Rats (male Wistar, 300-350 g) were subjected to two daily tests in a water maze, including a hidden platform (Morris, *J. Neurosci. Methods* 11:47-60 (1984) and Gordon et al., *Neurosci Lett.* 199:1-4 (1995); Gozes et al., *J. Neurobiol.* 33:329-342 (1997)). Every day for the first test, both the platform and the animal were situated in a new location with regard to the pool (with the pool being immobile). The experiment was performed as follows: the animal was positioned on the platform for 0.5 minutes then placed in the water. The time required to reach the platform (indicative of learning and intact reference memory) was measured (first test). After 0.5 minute on the platform, the animal was placed back in the water (in the previous position) for an additional second test and search for the hidden platform (retained in the previous position). The time required to reach the platform in the second trial was recorded, indicative of short-term (working) memory. All measurements were performed using the computerized video-assisted HVS water maze system (HVS Image Ltd. Hampton, UK). Animals were tested for four days to eliminate random memory defective animals. The best performers were injected i.c.v. at a rate of 0.21 µl/min. with the cholinotoxin ethylcholine aziridium (AF64A, 3 nmol12 µl/side), control animals received an injection of saline (Gozes et al., *Proc. Natl. Acad. Sci. USA* 93:427-432 (1996)).

Figure 14A:
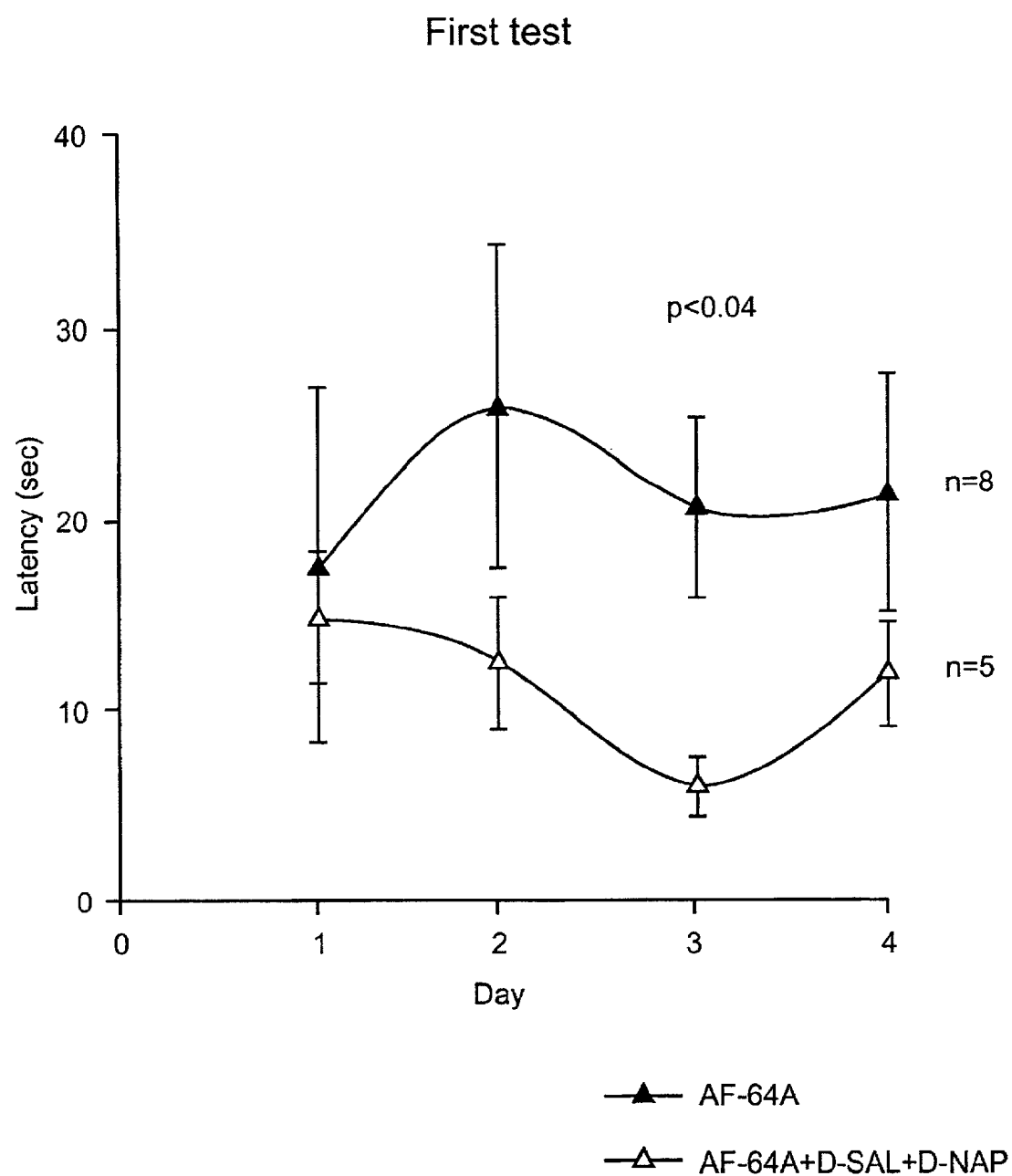
FIGS. 14A and B illustrate the effect of oral administration of D-NAPVSIPQ+D-SALLRSIPA on learning and memory in rats treated with the cholinotoxin AF-64A. Short-term memory processes were examined by performance in the Morris water maze, measuring the time required to find the hidden platform in the second of two daily trials. The platform location and the starting point in which the animal was placed in the water were held constant within each pair of daily trials, but both locations were changed every day. For the first test, both the platform and the animal were situated in a new location with regard to the pool (with the pool being immobile). The experiment was performed as follows: the animal was positioned on the platform for 0.5 minute, then placed in the water.
Figure 14B:
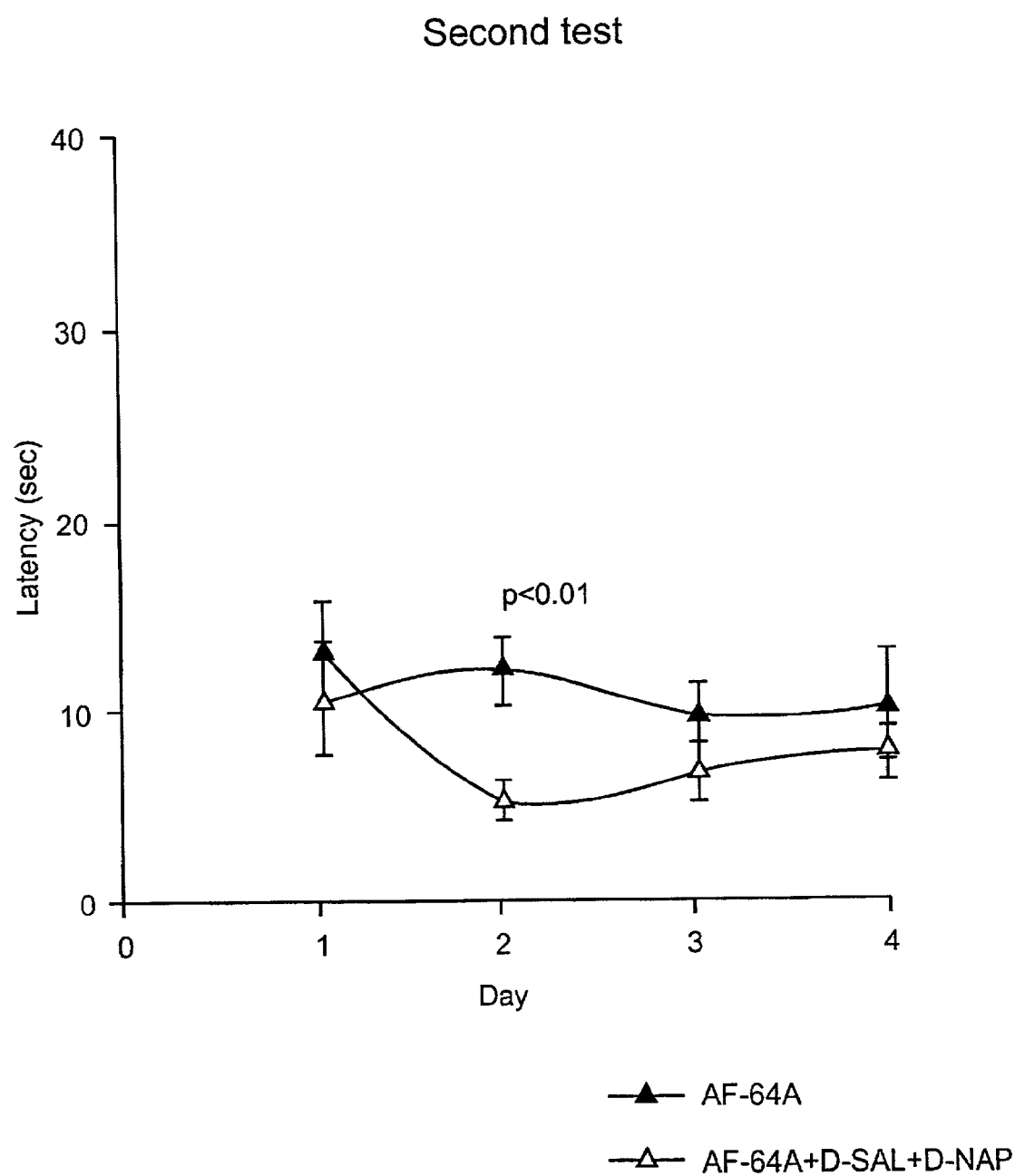
FIG. 14C illustrates the effect of oral administration of D-SALLRSIPA alone on learning and memory in rats treated with the cholinotoxin AF-64A.

Animals were allowed to recover for one week, followed by daily exposure to three micrograms of D-SAL+three micrograms of D-NAP, in 20 microliter saline, applied orally on the tongue. After a week of oral peptide application, the animals were subjected to two daily tests in the water maze (as above). During the test-period, animals were also given an oral administration of peptide or vehicle (carrier) an hour before the daily test. It was previously shown that AF64A-treated animals exhibit learning and memory deficits in the Morris water maze test (Gozes et al., *Proc. Natl. Acad Sci. USA* 93:427-432 (1996)). Here, AF64A-treated rats subjected to oral application of D-NAP+D-SAL exhibited a decreased latency in finding the hidden platform, indicative of improved reference memory (FIG. 14A, first daily test). Furthermore, the same rats exhibited improved working memory in the second daily test (FIG. 14B). These data indicate that oral administration of a combination of D-SAL and D-NAP resulted in significant increases in learning and memory in animals with chemically induced cholinergic impairment.

Figure 14C:
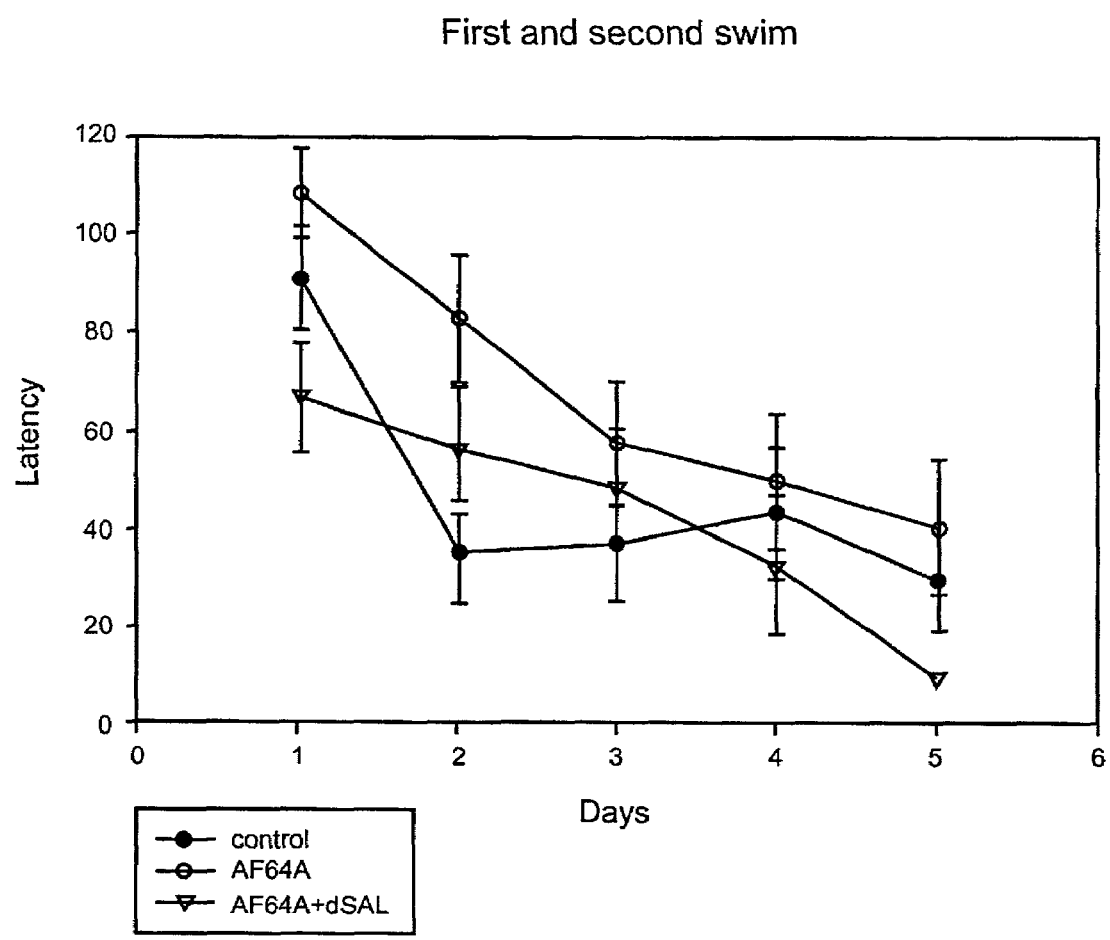

FIG. 14C illustrates the effect of oral administration of D-SALLRSIPA alone on learning and memory in rats treated with the cholinotoxin AF-64A. Rats were treated with the cholinotoxin AF-64A and D-SALLRSIPA as described in Gozes et al., *J. Pharmacol. Exp. Therap.* 293:1091-1098 (2000), except that D-SALLRSIPA was delivered to AF64A-treated rats was as follows: 10 microgram D-SALLRSIPA (D-SAL) per rat (250-300 g) per day in 50 microliter saline under the tongue, using a micropipette. Peptides were applied once daily for three days, a week after the AF64A lesion. After a 2-day cessation, peptides were applied once daily for another 5 days and tested from day three on. Following an additional two-day cessation, peptides were applied again daily for two days and tested in the Morris water maze. The graph shows the results of the 5 day testing. In each day the animals were subjected to two consecutive tests and results are a summation of the two daily tests. Significance (one way ANOVA with Student-Neuman-Kuels multiple comparison of means test) is as follows.

Day 1:$P<0.04$ D-SALLRSIPA-AF64A vs. AF64A;

Day 2:$P<0.04$ AF64A vs. control (sham operated), SALLRSIPA (SEQ ID NO:1) treatment was not significantly different from either AF64A animals or control, suggesting some improvement;

Day 3:No difference;

Day 4:No difference; and

Day 5:t-test: $P<0.04$ D-SALLRSIPA-AF64A vs. AF64A.

These results suggest that D-SALLRSIPA (D-SAL) is effective on its own.

4. Memory Improvements in ApoE-deficient Mice

Figure 15:
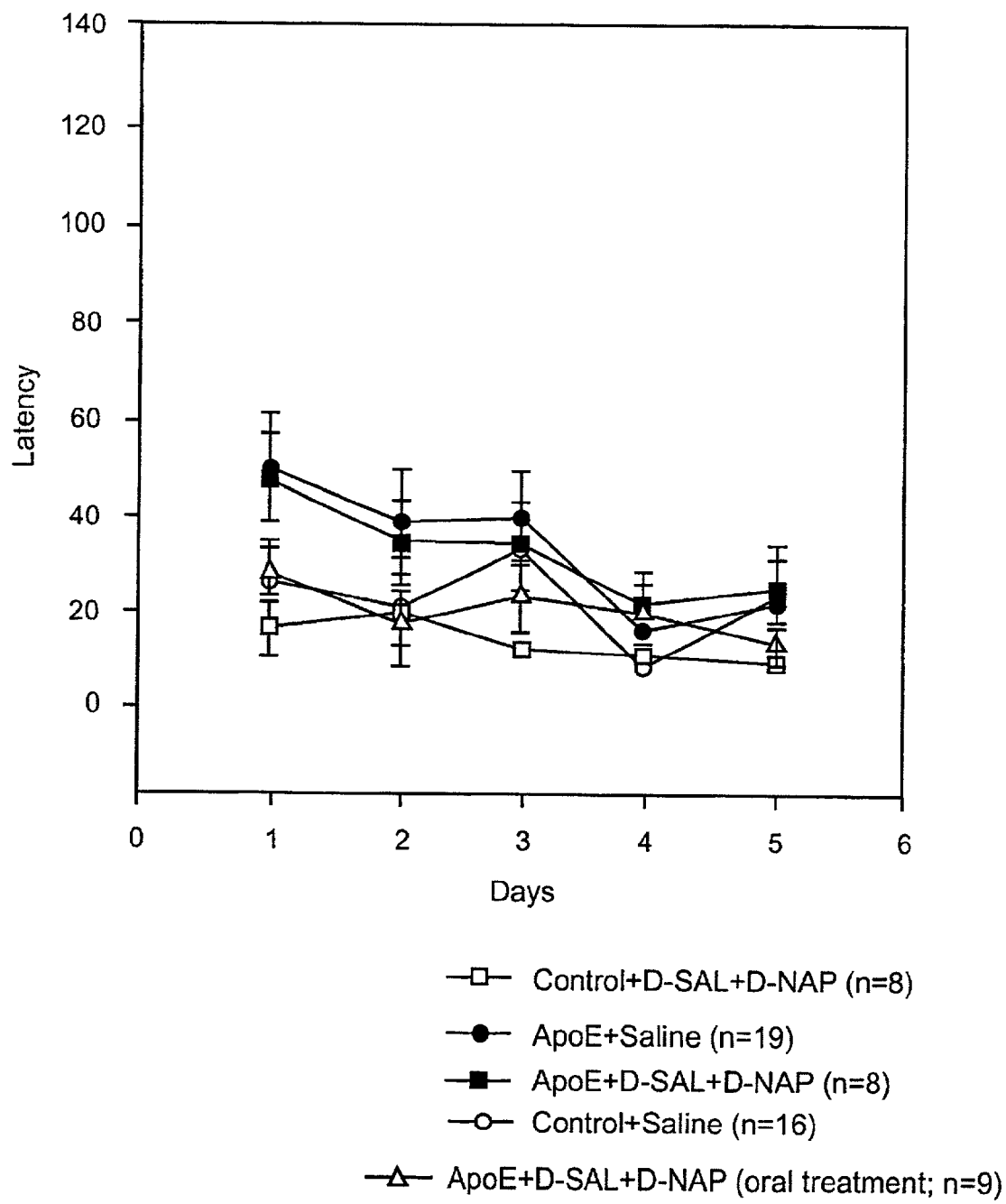
FIG. 15 illustrates comparison of sublingual (oral) and subcutaneous administration of D-SAL+D-NAP in control vs. Apo-E knock-out mice assessed for short-term memory in the Morris swim maze. Improvements of cognitive functions were observed a week after cessation of the 2-week daily D-SAL+D-NAP treatment, i.e., in 21-day-old mice exposed to a 5-day training protocol. The time required to find the hidden platform in the second of two daily trials was measured. The platform location and the starting point in which the animal was placed in the water were held constant within each pair of daily trials, but both locations were changed every day. On the second test of the first trial day, the ApoE-deficient mice were significantly retarded as compared to controls (P<0.04) and improved after oral application of D-SAL+D-NAP, with most of the treated animals finding the platform at a latency of ≦20 sec.

Memory deficits and cholinergic impairments have been described in adult ApoE-deficient mice. These deficits may mimic the conditions found in people that are homozygous for apolipoprotein E4, a condition that in which patients are more prone to an early onset of Alzheimer's disease, in contrast to people carrying the E2 or E3 alleles (Gordon et al., *Neurosci. Lett.* 199:1-4 (1995)). A week after cessation of treatment, cognitive functions were assessed in the Morris water maze. Improvements of cognitive functions were observed a week after cessation of the 2-week daily D-SAL-D-NAP treatment, i.e. in 21-day-old mice exposed to a 5-day training protocol (FIG. 15). Short-term memory processes were examined by performance in the water maze, measuring the time required to find the hidden platform in the second two daily trials. The platform location and the starting point in which the animal was placed in the water were held constant within each pair of daily trials, but both locations were changed every day. On the second test of the first trial day, the ApoE-deficient mice were significantly retarded as compared to controls ($P<0.04$) and improved after oral application of D-SAL+D-NAP, with most of the treated animals finding the platform at a latency of $\leq 20$ sec.

FIGS. 16A and 16B illustrate the first test and second test, respectively, of Morris water maze test results in apolipoprotein E-deficient mice. Experiments were performed following injections of a mixture of D-NAP-D-SAL with an injection protocol and Morris water maze as described in Gozes et al., *J. Pharmacol. Exp. Therap.* 293:1091-1098 (2000)). Results showed significant improvements on day 1 and day 2 (first daily test, and on day three, second daily test)—$P<0.05$.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. For example, any one or more of the features of the previously described embodiments can be combined in any manner with one or more features of any other embodiments in the present invention. The scope of the invention should, therefore, be determined not with reference to the above description, but instead should be determined with reference to the appended claims along with their full scope of equivalents.

What is claimed is:

1. An Activity Dependent Neurotrophic Factor I (ADNF I) polypeptide, the ADNF I polypeptide comprising an active core site having the following amino acid sequence:
Ser-Ala-Leu-Leu-Arg-Ser-Ile-Pro-Ala (SEQ ID NO:1), wherein each amino acid of SEQ ID NO:1 is a D-amino acid, and wherein the ADNF I polypeptide has neurotrophic/neuroprotective activity.

2. The ADNF I polypeptide of claim 1, wherein the ADNF I polypeptide consists of Ser-Ala-Leu-Leu-Arg-Ser-Ile-Pro-Ala (SEQ ID NO:1), wherein each amino acid is a D-amino acid.

3. The ADNF I polypeptide of claim 1, wherein the ADNF I polypeptide is selected from the group consisting of:
Val-Leu-Gly-Gly-Gly-Ser-Ala-Leu-Leu-Arg-Ser-Ile-Pro-Ala (SEQ ID NO:14);
Val-Glu-Glu-Gly-Ile-Val-Leu-Gly-Gly-Gly-Ser-Ala-Leu-Leu-Arg-Ser-Ile-Pro-Ala (SEQ ID NO:15);
Leu-Gly-Gly-Gly-Ser-Ala-Leu-Leu-Arg-Ser-Ile-Pro-Ala (SEQ ID NO:16);
Gly-Gly-Gly-Ser-Ala-Leu-Leu-Arg-Ser-Ile-Pro-Ala (SEQ ID NO:17);
Gly-Gly-Ser-Ala-Leu-Leu-Arg-Ser-Ile-Pro-Ala (SEQ ID NO:18); and
Gly-Ser-Ala-Leu-Leu-Arg-Ser-Ile-Pro-Ala (SEQ ID NO:19),
wherein each amino acid of the active core site Ser-Ala-Leu-Leu-Arg-Ser-Ile-Pro-Ala (SEQ ID NO:1) is a D-amino acid and additional amino acids are D or L amino acids.

4. The ADNF I polypeptide of claim 1, wherein the ADNF I polypeptide comprises up to about 20 amino acids at each of an N-terminus and a C-terminus of the active core site.

5. The ADNF I polypeptide of claim 4, wherein both N-terminal and C-terminal amino acids of the ADNF I polypeptide are D-amino acids.

6. A pharmaceutical composition comprising a pharmaceutically acceptable excipient and the Activity Dependent Neurotrophic Factor I (ADNF I) polypeptide of claim 1.

7. The pharmaceutical composition of claim 6, wherein the ADNF I polyptptide consists of Ser-Ala-Leu-Leu-Arg-Ser-Ile-Pro-Ala (SEQ ID NO:1), wherein each amino acid is a D-amino acid.

8. The pharmaceutical composition of claim 6, wherein the composition is formulated for intranasal, intraperitoneal, subcutaneous, gavage, sublingual, intravenous, or oral administration.

9. The pharmaceutical composition of claim 6, wherein the composition is formulated for oral administration.

10. A method for reducing neuronal cell death, the method comprising contacting the neuronal cells with an Activity Dependent Neurotrophic Factor I (ADNF I) polypeptide of claim 1 in an amount sufficient to prevent neuronal cell death.

11. The method of claim 10, wherein the ADNF I polypeptide consists of Ser-Ala-Leu-Leu-Arg-Ser-Ile-Pro-Ala (SEQ ID NO:1), wherein each amino acid is a D-amino acid.

12. The method of claim 10, wherein the neuronal cells are selected from the group consisting of spinal cord neurons, hippocampal neurons, cerebral cortical neurons and cholinergic neurons.

* * * * *

UNITED STATES PATENT AND TRADEMARK OFFICE
CERTIFICATE OF CORRECTION

PATENT NO.         : 7,384,908 B1
APPLICATION NO.    : 10/049587
DATED              : June 10, 2008
INVENTOR(S)        : Douglas E. Brenneman et al.

It is certified that error appears in the above-identified patent and that said Letters Patent is hereby corrected as shown below:

On the title page, item [73]: please delete "National Institute of Health"

and insert -- The Government of the United States of America as Represented by the Secretary of the Department of Health and Human Services --

Signed and Sealed this

Seventh Day of April, 2009

JOHN DOLL
*Acting Director of the United States Patent and Trademark Office*